United States Patent
Worrell

(10) Patent No.: US 11,020,171 B2
(45) Date of Patent: Jun. 1, 2021

(54) ELECTROSURGICAL INSTRUMENT WITH PASSIVE ARTICULATION AND THERMAL INSULATION

(71) Applicant: Ethicon LLC, Guaynabo, PR (US)

(72) Inventor: Barry Worrell, Centerville, OH (US)

(73) Assignee: Ethicon LLC, Guaynabo, PR (US)

( * ) Notice: Subject to any disclaimer, the term of this patent is extended or adjusted under 35 U.S.C. 154(b) by 1158 days.

(21) Appl. No.: 15/422,123

(22) Filed: Feb. 1, 2017

(65) Prior Publication Data

US 2018/0214199 A1    Aug. 2, 2018

(51) Int. Cl.
| | |
|---|---|
| *A61B 18/14* | (2006.01) |
| *A61B 17/29* | (2006.01) |
| *A61B 17/295* | (2006.01) |
| *A61B 18/00* | (2006.01) |

(52) U.S. Cl.
CPC .......... *A61B 18/1445* (2013.01); *A61B 17/29* (2013.01); *A61B 17/295* (2013.01); *A61B 2017/2905* (2013.01); *A61B 2017/2908* (2013.01); *A61B 2017/2946* (2013.01); *A61B 2018/00101* (2013.01); *A61B 2018/1455* (2013.01)

(58) Field of Classification Search
CPC ....... A61B 17/29; A61B 17/295; A61B 18/14; A61B 18/1442; A61B 18/1445; A61B 18/1448; A61B 2017/2905; A61B 2017/2908; A61B 2017/2946; A61B 2018/00101; A61B 2018/1455
USPC ..................................................... 606/51–52
See application file for complete search history.

(56) References Cited

U.S. PATENT DOCUMENTS

| | | | |
|---|---|---|---|
| 8,579,176 B2 | 11/2013 | Smith et al. | |
| 8,672,951 B2 | 3/2014 | Smith et al. | |
| 9,161,803 B2 | 10/2015 | Yates et al. | |
| 9,554,803 B2 | 1/2017 | Smith et al. | |
| 2006/0217709 A1* | 9/2006 | Couture | A61B 18/1442 606/51 |
| 2007/0221700 A1* | 9/2007 | Ortiz | A61B 34/71 227/175.1 |
| 2009/0171354 A1* | 7/2009 | Deville | A61B 18/1445 606/51 |

(Continued)

*Primary Examiner* — Michael F Peffley
*Assistant Examiner* — Khadijeh A Vahdat
(74) *Attorney, Agent, or Firm* — Mintz Levin Cohn Ferris Glovsky and Popeo, P.C.

(57) ABSTRACT

Electrosurgical instruments with passive articulation and thermal insulation are described herein. Such instruments can provide the advantages associated with passive articulation while protecting tissue and other structures from unintentional thermal damage when an end effector is pressed thereagainst to effect articulation while at an elevated temperature due to use. In one embodiment, such an instrument can include a distal end effector with jaws to clamp tissue, a proximal actuating portion, an energy delivery surface that contacts grasped tissue, and a passive articulating portion disposed between the end effector and the actuating portion. The articulating portion can be configured to selectively permit movement of the end effector relative to the actuating portion in response to external forces acting on the end effector. Further, an outward-facing surface of at least one of the first and second jaws can be covered in a thermally insulating material.

21 Claims, 17 Drawing Sheets

(56) References Cited

U.S. PATENT DOCUMENTS

2012/0078139 A1    3/2012  Aldridge et al.
2012/0078247 A1    3/2012  Worrell et al.
2014/0005681 A1*   1/2014  Gee ................ A61B 17/320092
                                                          606/130
2015/0209573 A1    7/2015  Hibner et al.

* cited by examiner

ELECTROSURGICAL INSTRUMENT WITH PASSIVE ARTICULATION AND THERMAL INSULATION

FIELD

This disclosure relates generally to surgical instruments and, more particularly, to electrosurgical instruments that can be passively articulated.

BACKGROUND

A variety of surgical instruments are employed in various open, endoscopic, and laparoscopic surgeries. One group of such instruments is utilized to manipulate tissue, seal tissue, and/or transect tissue. These instruments can include a distal end effector having opposed jaw members that move relative to one another to grasp tissue therebetween. Certain of these instruments can also include a cutting mechanism that can be advanced through the grasped tissue to transect it. Electrical or other energy can also be delivered to the grasped tissue to seal the tissue prior to, or concurrent with, transection. For example, electrical energy can be applied to the grasped tissue by various mono-polar and bi-polar radio frequency (RF) electrodes or other energy delivery structures coupled to the jaw members. In other embodiments, ultrasonic energy can be applied to tissue by oscillating an energy delivery surface or structure to effect tissue sealing and transection.

These surgical instruments often include a proximal actuating portion from which the distal end effector can be controlled. The proximal actuating portion can include a plurality of actuators, such as triggers or other mechanisms to control the various functions of the instrument. For example, a first trigger can control the opening or closing of the jaw members to grasp tissue, while a second trigger can control the operation of a cutting mechanism and/or the delivery of energy to seal tissue. In use, a user can actuate the first trigger and hold or latch it in an actuated or closed position to securely grasp and compress tissue between the first and second jaw members, then the user can actuate the second trigger to transect and/or seal the tissue.

Often such surgical instruments are utilized in procedures where access to a surgical site can be limited. For example, in certain minimally invasive procedures surgical instruments are passed into a patient's body through, for example, a trocar or natural orifice that has a limited size opening through which the instrument can pass. Moreover, the trocar or natural orifice cannot be easily repositioned during the procedure, such that certain areas not directly aligned with the opening or working channel through which the instrument is passed can be inaccessible.

To provide greater utility in such situations, certain surgical instruments can also include an articulating portion that allows the end effector to be moved relative to the actuating portion. For example, an articulating portion can be included in some instruments along the length of a shaft that connects the distal end effector to the proximal actuating portion. The articulating portion can permit the end effector to be positioned such that a longitudinal axis of the end effector is transverse, or non-parallel, to a longitudinal axis of the actuating portion or the shaft extending therefrom. The ability to articulate the end effector relative to the actuating portion can be valuable, as it can permit the instrument to access tissue and perform surgical operations that might not otherwise be possible, or at least might be more difficult or physically awkward to perform with a straight shaft instrument.

A variety of different articulating portion configurations are known. For example, "active" articulating devices can include an articulating portion and one or more mechanisms for causing movement of the end effector relative to the proximal actuating portion. By way of further example, active articulating devices can include push/pull wires extending from the end effector to the proximal actuating portion, as well as any of gear trains, racks, levers, and other mechanical components and a motor or other force generator to actuate the push/pull wires and cause articulation of the end effector.

Another group of articulating devices makes use of external forces to provide actuating force for articulation. Such devices, referred to generally as "passive" articulating devices, often have end effectors that can be locked in a particular position/orientation, or unlocked to allow articulation to a different position/orientation. Such devices, however, can omit the levers, motors, gear trains, or other actuating components that cause articulation of the end effector in an active articulating device. Instead, passive articulating devices can rely on a user pressing the end effector against an outside structure, e.g., an anatomical structure at a surgical site, to cause the end effector to articulate into a new desired position/orientation. Once in the desired position/orientation, the end effector can be locked and the instrument used to, e.g., grasp, seal, cut, etc. tissue. In some embodiments, passive articulating devices can be biased to a "home" position/orientation (e.g., a neutral or centered position/orientation) such that a biasing force must be overcome to articulate the end effector and, once articulated, a user can return the device to the home position/orientation by simply unlocking the end effector.

Surgical instruments equipped with passive articulating portions can have advantages over other articulating instruments. For example, passive articulating devices can have fewer components than other devices, e.g., devices having powered or otherwise actively controlled articulating portions. Having fewer components can result in the devices being less expensive and less prone to failure than other devices. Such devices can also be physically smaller and therefore able to access surgical sites through smaller diameter trocars, etc.

Passive articulating devices that also utilize energy delivery to cut and/or seal tissue can have particular disadvantages as well, though. For example, delivering electrical energy to tissue through one or more electrodes or other energy delivery surfaces or structures coupled to the end effector can create large amounts of heat capable of damaging tissue. Indeed, tissue sealing is accomplished through intentional heating of tissue grasped by the end effector (e.g., clamped between end effector jaws). Energy delivery can also cause the remainder of the end effector to become dangerously hot, however, as it is typically formed of a material having good thermal conductivity, such as a metal, etc. When the end effector is raised to a temperature capable of damaging tissue upon contact, unintentional tissue damage can be inflicted as the end effector is pressed against an anatomical structure in order to effect passive articulation during use. This problem is somewhat unique to passive articulating devices that deliver energy to cut to seal tissue using heat. That is, other types of surgical instruments that do not deliver energy to tissue, such as staplers, etc., do not encounter problems associated with the end effector being hot enough to damage tissue during passive articulation maneuvers.

Accordingly, there is a need in the art for improved passive articulating surgical instruments or devices. More particularly, there is a need for improved passive articulating devices that are configured to deliver energy to tissue to create localized heating for transection and/or sealing.

SUMMARY

The present disclosure generally provides improved passive articulation instruments and methods that protect an outer surface of an end effector with a thermally insulating material such that the end effector does not inflict unintentional tissue damage when it is pressed against anatomical structures during articulation. The use of a thermally insulating material on an outer surface of the end effector can isolate the internal end effector components that are at an elevated temperature from contacting adjacent tissue during passive articulation. As a result, the instruments and methods described herein can more effectively isolate heating of tissue to desired areas, e.g., tissue clamped between jaw members of an end effector that is targeted for transection and/or sealing, and prevent collateral damage to adjacent tissue.

In one aspect, a surgical instrument is provided that can include a distal end effector having a first jaw and a second jaw that are movable relative to one another between an open position and a closed position to clamp tissue therebetween, a proximal actuating portion, an energy delivery surface coupled to the end effector such that the energy delivery surface contacts tissue clamped between the first and second jaws when in the closed position, and a passive articulating portion disposed between the end effector and the actuating portion. The articulating portion can be configured to selectively permit movement of the end effector relative to the actuating portion in response to external forces acting on the end effector. Further, an outward-facing surface of at least one of the first and second jaws can be covered in a thermally insulating material.

The instruments and methods described herein can have a number of additional features and/or variations, all of which are within the scope of the present disclosure. In some embodiments, for example, the thermally insulating material can be a polymer, such as a high-temperature polyamide (e.g., Thermec N™, a glass-filled nylon). In other embodiments, alternative materials can be utilized, such as alumina compounds, yttria-stabilized zirconia (YSZ), or poly-para-xylylene polymers, such as Parylene™. In some embodiments, these materials can be applied by plasma or spray treatment, or physical or chemical vapor deposition. Moreover, the thermally insulating material can have a variety of thicknesses, depending upon a desired level of thermal insulation. In some embodiments, for example, the thermally insulating material can have a thickness between about 0.15 mm and about 1 mm.

The thermally insulating material can be formed on the outward-facing surface of at least one of the first and second jaws in a variety of manners. For example, in some embodiments the thermally insulating material can be sprayed onto the outward-facing surface of at least one of the first and second jaws. In other embodiments, the thermally insulating material can be overmolded onto at least one of the first and second jaws. In still other embodiments, the thermally insulating material can be formed separately and coupled to an outward-facing surface of at least one of the first and second jaws, e.g., using an interference fit, adhesive, mechanical fasteners, etc.

In certain embodiments, the instrument can also include a cutting element coupled to the end effector and configured to transect tissue clamped between the first and second jaws when in the closed position. The cutting element can be, for example, a beam or blade that can be configured to translate along a length of the end effector to transect tissue grasped between the first and second jaws. In some embodiments, the cutting element can also act as a closure element that exerts force on the first and second jaws to move them from an open position to a closed position.

In some embodiments, the instrument can further include an articulation control band coupled to the end effector that extends proximally through the passive articulating portion and into the proximal actuator portion. Movement of the end effector relative to the proximal actuating portion about the passive articulating portion can cause longitudinal translation of the articulation control band. As a result, selective restraint of the articulation control band at the proximal actuating portion can effect selective locking of the passive articulating portion. To this end, in some embodiments the instrument can further include an articulation locking actuator disposed within the proximal actuator portion. The articulation locking actuator can be configured to selectively restrain the articulation control band to selectively permit movement of the end effector relative to the actuating portion in response to external forces acting on the end effector. Still further, in some embodiments the instrument can further include a second articulation control band and the articulation locking actuator can be configured to selectively restrain each articulation control band.

In certain embodiments, the instrument can further include a tissue clamping actuator configured to control movement of the first and second jaws of the end effector. And in some embodiments the instrument can also include an energy delivery actuator configured to control delivery of energy to tissue through the energy delivery surface of the end effector.

In another aspect, a surgical instrument is provided that can include a distal end effector having a first jaw and a second jaw that are movable relative to one another between an open position and a closed position to clamp tissue therebetween, wherein an outward-facing surface of at least one of the first and second jaw members is covered in a thermally insulating material. The instrument can further include a proximal actuating portion with a shaft extending distally therefrom, at least one electrode coupled to the end effector such that the electrode contacts tissue clamped between the first and second jaw members when in the closed position, and a passive articulating portion coupled to a proximal end of the end effector and a distal end of the shaft. The passive articulating portion can include a plurality of articulation control bands extending through the shaft to the proximal actuating portion. Moreover, each of the plurality of articulation control bands can be coupled to a locking element that is disposed within the proximal actuating portion and that has at least one mating feature formed on a surface thereof. The proximal actuating portion can further include an articulation locking actuator biased toward a first position and movable to a second position. The articulation locking actuator can have a plurality of mating features formed on a surface thereof that are configured to engage with the at least one mating feature formed on the surface of each locking element when in the first position to prevent movement of the plurality of articulation control bands, and the articulation locking actuator can be further configured to separate from each locking element when in the second position to permit movement of the plurality of articulation control bands.

As with the instrument described above, a number of variations and additional features are possible. For example, in some embodiments each locking element can have a substantially cylindrical shape and the at least one surface feature can be a thread. Moreover, in some embodiments the articulation locking actuator can include a rack having a threaded surface configured to interface with the thread formed on the locking element.

In certain embodiments, the instrument can include one or more of the additional features mentioned above. For example, in some embodiments, the instrument can further include a cutting element coupled to the end effector and configured to transect tissue clamped between the first and second jaws when in the closed position. In other embodiments, the instrument can include a tissue clamping actuator configured to control movement of the first and second jaws of the end effector. In still other embodiments, the instrument can include an energy delivery actuator configured to control delivery of energy to tissue through the energy delivery surface of the end effector.

Surgical methods are also disclosed herein. Such methods can include, for example, grasping tissue between a first jaw and a second jaw of an end effector by actuating a proximal portion of a surgical instrument coupled to the end effector, passing energy through the tissue grasped between the first and second jaws of the end effector using an energy delivery surface that contacts the tissue grasped between the first and second jaws, releasing an articulation locking mechanism disposed in the proximal portion to permit movement of a passive articulating portion disposed between the end effector and the proximal portion, and pressing a thermally insulated outer surface of the end effector against an external structure to cause movement of the end effector relative to the proximal portion about the passive articulating portion.

In some embodiments, a surgical method can further include releasing tissue grasped between the first and second jaws. Tissue can be released, in some embodiments for example, prior to pressing the end effector against tissue to cause movement of the end effector. In other embodiments, the method can further include actuating the articulation locking mechanism to hold the end effector in position relative to the proximal portion. The articulation locking mechanism can be actuated, for example, once a desired level of articulation of the end effector has been achieved by pressing the end effector against tissue to cause movement of the end effector relative to the proximal portion about the passive articulating portion.

In certain embodiments, the energy delivery surface can be an electrode and passing energy through the tissue can include delivering electrical energy through the electrode. Electrical energy can be, for example, radio frequency (RF) electrical energy delivered from a generator to the electrode via one or more conductors. Moreover, in some embodiments the external structure can be any of tissue and another instrument, such as a grasper, retractor, or scope.

In some embodiments, releasing the articulation locking mechanism can include moving an articulation locking actuator against a biasing force from a first position, in which the actuator is engaged with a plurality of locking elements that are coupled to the passive articulating portion via a plurality of articulation control bands, to a second position, in which the actuator is separated from the plurality of locking elements.

Any of the features or variations described above can be applied to any particular aspect or embodiment of the disclosure in a number of different combinations. The absence of explicit recitation of any particular combination is due solely to the avoidance of repetition in this summary.

DETAILED DESCRIPTION

Certain exemplary embodiments will now be described to provide an overall understanding of the principles of the structure, function, manufacture, and use of the instruments and methods disclosed herein. One or more examples of these embodiments are illustrated in the accompanying drawings. Those skilled in the art will understand that the instruments and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present application. To the extent features are described herein as being a "first feature" or a "second feature," such numerical ordering is generally arbitrary, and thus such numbering can be interchangeable.

Additionally, to the extent that linear or circular dimensions are used in the description of the disclosed instruments and methods, such dimensions are not intended to limit the types of shapes that can be used in conjunction with such instruments and methods. A person skilled in the art will recognize that an equivalent to such linear and circular dimensions can easily be determined for any geometric shape. Still further, sizes and shapes of the instruments, and the components thereof, can depend at least on the anatomy of the subject in which the instruments will be used, the size and shape of components with which the instruments will be used, and the methods and procedures in which the instruments will be used.

Surgical instruments and methods are described herein that provide passive articulation instruments and methods that protect an outer surface of an end effector with a thermally insulating material such that the end effector does not inflict unintentional tissue damage when it is pressed against anatomical structures during articulation. Use of a thermally insulating material on an outer surface of an end effector of such instruments or devices can more effectively isolate heating of tissue to desired areas and prevent collateral damage to adjacent tissue.

Figure 1:
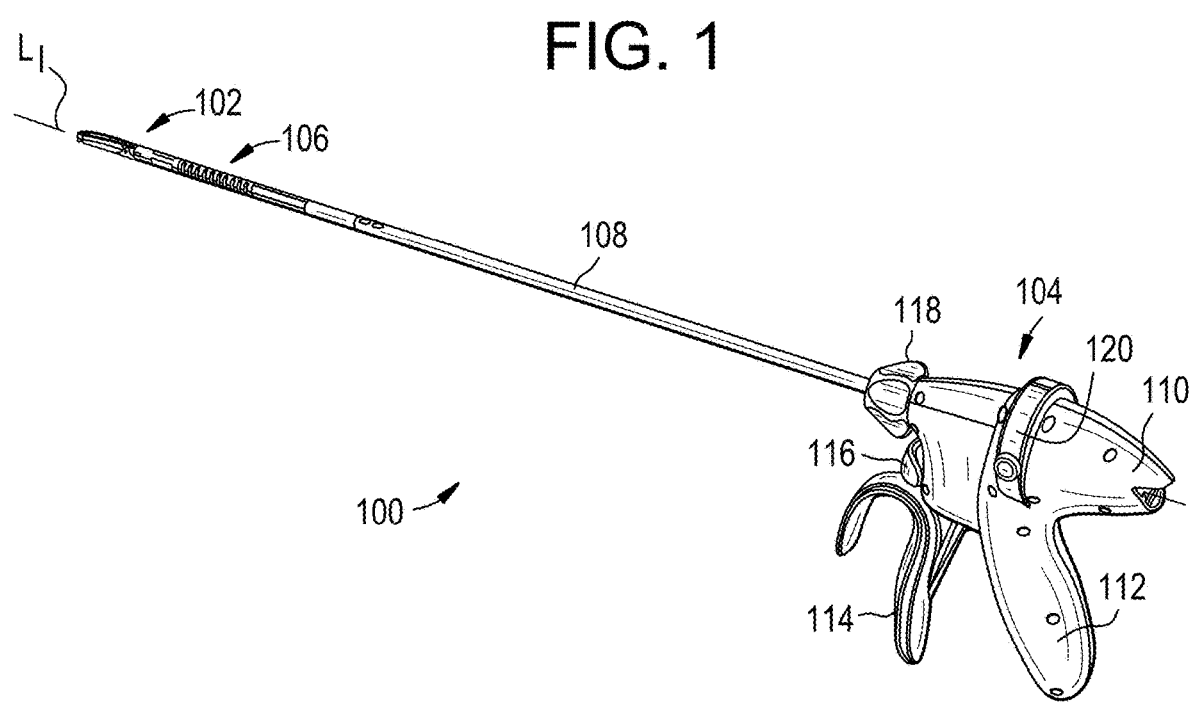
FIG. 1 is a perspective view illustration of one embodiment of a surgical instrument according to the teachings provided herein.

FIG. 1 illustrates one embodiment of a surgical instrument 100 according to the teachings provided herein. The instrument 100 includes an end effector 102 at a distal end thereof, as well as a proximal actuating portion 104 configured to control operation of the end effector. The instrument can also include an articulating portion 106 disposed between the end effector 102 and the actuating portion 104 that is configured to allow movement of the end effector 102 relative to the proximal actuating portion. Also disposed between the end effector 102 and the actuating portion 104 can be a shaft 108. The articulating portion 106 can be disposed anywhere along the length of the shaft 108 and, as in the illustrated embodiment, can be positioned in some embodiments adjacent to the end effector 102.

The proximal actuating portion 104 can have a variety of forms, including forms configured for interfacing with a human user and forms configured for interfacing with a robotic surgery platform. In the illustrated embodiment, the actuating portion 104 includes a housing 110 having a pistol grip 112 configured to interface with a user's hand. The actuating portion 104 also includes a first actuator in the form of a first trigger 114 and a second actuator in the form of a second trigger 116. The first and second actuators can perform various functions and, as explained in more detail below, in some embodiments the first trigger 114 can control opening and closing of opposed jaw members of the end effector 102, while the second trigger 116 can control delivery of electrical energy to tissue disposed between the opposed jaw members to effect tissue sealing. The pistol grip 112, first trigger 114, and second trigger 116 can be modified, substituted, supplemented, etc. in any suitable way, and descriptions of such components herein are merely illustrative.

The proximal actuating portion 104 can also include additional actuators, such as a rotation control 118 that can be used to rotate the end effector about a longitudinal axis $L_I$ of the instrument 100. The actuating portion 104 can further include an articulation control 120 that can be used to selectively lock and unlock the position and/or orientation of the end effector 102 relative to any of the shaft 108 and the actuating portion 104. In an unlocked configuration, a user can effect articulation of the end effector 102 by pressing an outer surface of the end effector against an outside structure, such as a nearby anatomic structure, during a procedure. Alternatively, the end effector can be pressed against some other structure external to the instrument, including another instrument, such as a grasper, trocar, retractor, camera, etc. When a desired position and/or orientation of the end effector 102 is reached, the articulation control 120 can be utilized to selectively lock the position and/or orientation of the end effector 102. The process can be repeated in reverse in some embodiments to realign the end effector 102 in the orientation shown in FIG. 1. In other embodiments, the end effector 102 can be biased to the centered orientation of FIG. 1 such that it can return to this orientation without the need for interacting with an external structure when the articulation control 120 is utilized to move to an unlocked configuration while the end effector is articulated (as shown, e.g., in FIG. 4).

Figure 2:
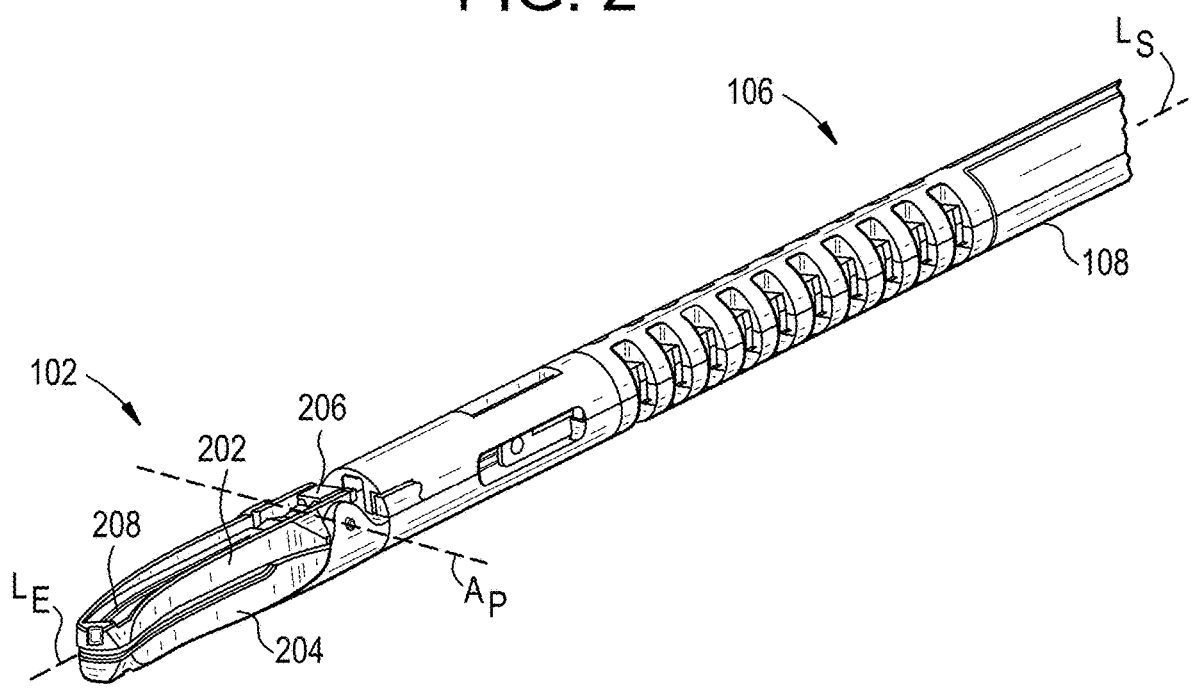
FIG. 2 is a perspective detail view of a distal portion of the surgical instrument of FIG. 1 with an end effector in a closed position.

FIG. 2 illustrates a closer view of a distal portion of the instrument 100. There are a number of possible configurations of the end effector 102 but, in one embodiment, the end effector can include a first jaw 202 and a second jaw 204 that can be pivotably coupled to one another and configured to rotate relative to one another about a pivot axis $A_p$. Depending upon the particular embodiment, both the first and second jaws 202, 204 can move relative to one another or, as in the illustrated embodiment, the second jaw 204 can be substantially fixed while the first jaw 202 can pivot about the pivot axis $A_p$ toward and away from the second jaw 204.

In some embodiments, one or more actuators, such as rods, cables, bands, etc., can extend from the proximal actuator portion 104 and can be joined with the first jaw 202 such that longitudinal and/or rotational movement of the actuator rods, cables, bands, etc., can control pivoting of the first jaw 202 relative to the second jaw 204. Of course, the first and second jaws 202, 204 can instead have any other suitable kind of movement and can be actuated in any other suitable fashion.

As seen in FIGS. 2 and 6-8, the instrument 100 can include an actuating beam 206 that is longitudinally movable along part of the length of the end effector 102. The actuating beam 206 can be coaxially positioned within the shaft 108, can extend along the length of the shaft, and can translate longitudinally within the shaft (including the articulating portion 106), though it should be understood that the actuating beam and the shaft can have any other suitable relationship. The actuating beam 206 can include a sharp distal blade integrally formed therein or coupled thereto, thereby making the actuating beam effective as a cutting element or mechanism. In some embodiments, this can be the sole purpose of the actuating beam 206, while in other embodiments the actuating beam 206 can also function to exert a force on the first and second jaws 202, 204 to urge them between their open and closed configurations. The distal blade of the actuating beam 206 can be substantially sharp, such that the distal blade will readily sever tissue that is captured between the first and second jaws 202, 204, thereby enabling the actuating beam to serve as a cutting element or mechanism for transecting tissue grasped by the first and second jaws. The actuating beam 206 can also be electrically grounded in some embodiments to provide a return path for RF or other energy delivered to tissue. In some embodiments, the distal blade of the actuating beam 206 can serve as an active electrode. In still other embodiments, the actuating beam 206 can be configured to oscillate when energized with ultrasonic energy (e.g., harmonic vibrations at approximately 55.5 kHz, etc.). Examples of applying energy are described further in U.S. Pat. Pub. No. 2012/0078139; U.S. Pat. No. 9,161,803; and U.S. Pat. Pub. No. 2015/0209573, the entire contents of which are hereby incorporated by reference.

The actuating beam 206 can be configured to translate along a length of the end effector 102 within a slot 208 formed in the first jaw 202. A complementary slot 304 (see FIGS. 3 and 7) can be formed in the second jaw 204. In some embodiments, the actuating beam 206 can include an upper flange 701 (see FIG. 7) and a lower flange (not shown) that can ride along an upper and lower surface of the first and second jaws 202, 204, with the cutting element extending between the flanges and through the slots 208, 304 formed in the first and second jaws. Such a configuration can provide an "I-beam" type of cross section at a distal end of the actuating beam 206. While the upper flange 701 is shown in the figures extending longitudinally only along a small portion of the length of the actuating beam 206, in some embodiments the flanges can extend longitudinally along any suitable length of the actuating beam 206. In addition, while the flange 701 is shown in the figures positioned along the exterior of the first jaws 202, the flanges can alternatively be disposed in corresponding slots formed within the first and second jaws 202, 204. For instance, each jaw 202, 204 can define a "T"-shaped slot, with parts of the cutting element of the actuating beam 206 being disposed in one vertical portion of each "T"-shaped slot and with the flanges being disposed in the horizontal portions of the "T"-shaped slots. There are a variety of other suitable configurations and relationships that can also be utilized in connection with the teachings provided herein.

As noted above, the "I-beam" type of configuration of the actuating beam 206 can also provide closure of the first and second jaws 202, 204 as the actuating beam is advanced distally. In particular, the flange 701 can urge the first jaw 202 pivotally toward the second jaw 204 as the actuating beam 206 is advanced from a proximal position to a distal position by bearing against the upper surface of the first jaw 202. The corresponding bottom flange (not shown) can similarly bear against the bottom surface of the second jaw 204 to prevent the actuating beam 206 from translating radially (i.e., in a direction perpendicular to a longitudinal axis of the actuating beam). The closing effect on the first and second jaws 202, 204 by the actuating beam 206 can occur before the distal blade of the actuating beam reaches tissue captured between the first and second jaws in certain embodiments. Staggering encounters by the actuating beam 206 can reduce the force required to squeeze a trigger (e.g., the first trigger 114) to move the actuating beam 206 through a full firing stroke. In other embodiments, staggering the effects of actuating beam translation can allow separate triggers to control the processes of grasping and transecting tissue.

In certain embodiments, the flange 701 can be configured to cam against a ramp feature at a proximal end of the second jaw 204 to open the first and second jaws 202, 204 when the actuating beam 206 is retracted to a proximal position and to hold the first and second jaws open when the actuating beam 206 remains at the proximal position. This camming capability can facilitate use of the end effector 102 to separate layers of tissue, i.e., to perform blunt dissections, etc., by forcing the first and second jaws 202, 204 apart from a closed position. In some embodiments, the first and second jaws 202, 204 can be resiliently biased to an open position by a spring or other type of resilient feature. While the first and second jaws 202, 204 can close or open as the actuating beam 206 is translated in some embodiments, it should be understood that other embodiments can provide independent movement of the first and second jaws 202, 204 and the actuating beam 206. By way of example only, one or more cables, rods, beams, bands, or other features can extend through the shaft 108 to selectively actuate the first and second jaws 202, 204 independently of the actuating beam 206. Such jaw actuation features can be separately controlled by a dedicated feature of the proximal actuating portion 104 or can be controlled along with one or more other functions by a single trigger or actuating element. It should also be understood that the actuating beam 206 can be resiliently biased to a proximal position, such that the actuating beam retracts proximally when a user releases a trigger or other actuating element controlling the advancement of the actuating beam.

Figure 3:
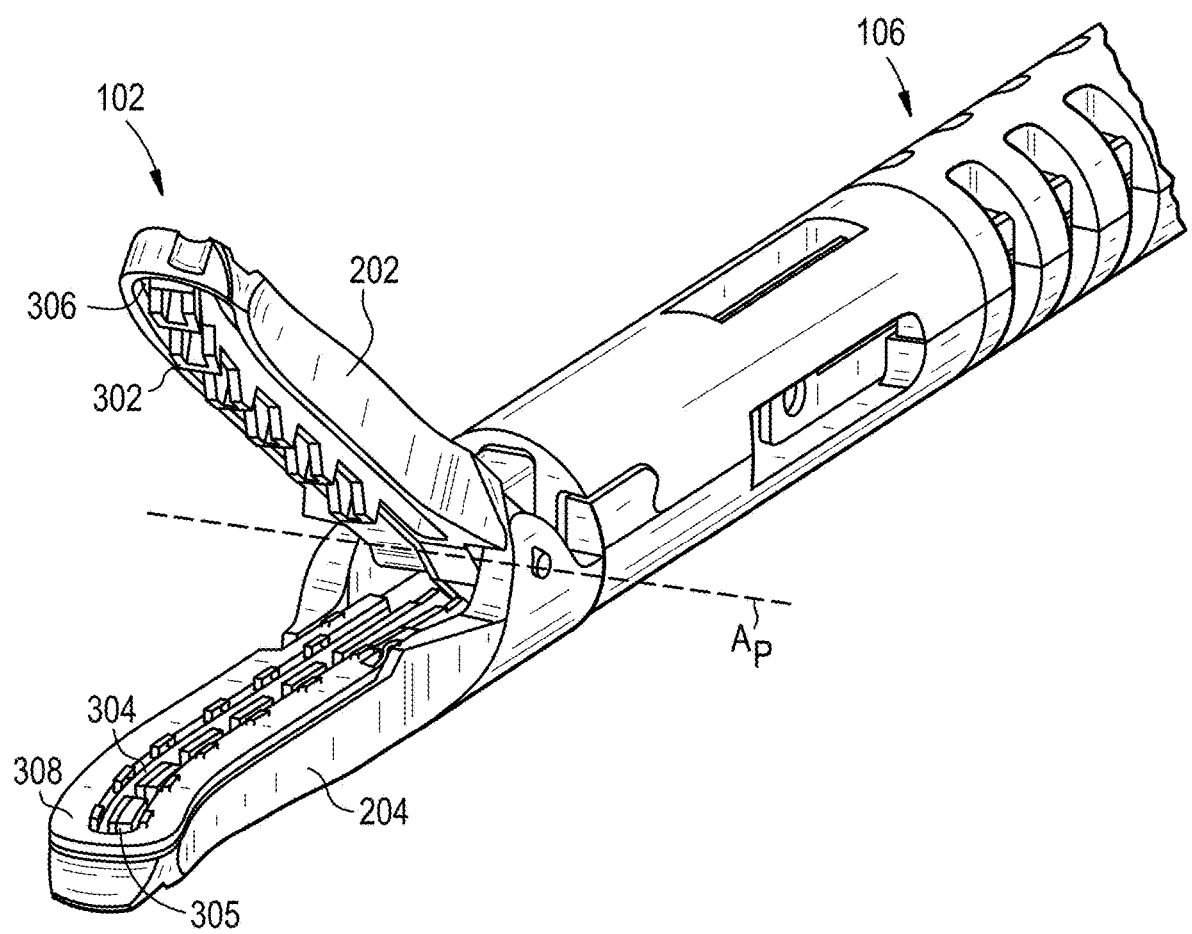
FIG. 3 is an alternative perspective detail view of the distal portion of the surgical instrument of FIG. 1 with the end effector in an open position.

FIG. 3 shows the end effector 102 in an open configuration in which the first jaw 202 is pivoted away from the second jaw 204. As visible in the figure, the first and second jaws 202, 204 can each include one or more features formed thereon that can be configured to facilitate more secure gripping of tissue when the first and second jaws are moved to the closed configuration of FIG. 2. Any of a variety of features, such as variously-shaped protrusions, recesses, etc. can be included, or the features can be omitted entirely. In the illustrated embodiment, a plurality of tooth-like protrusions 302 formed on the first jaw 202 and a plurality of complementary recesses 305 formed in the second jaw 204. These features can interact to more securely grip tissue between the first and second jaws 202, 204 and prevent tissue from, for example, sliding between the first and second jaws when they are in a closed configuration. In some embodiments, the protrusions 302 and/or recesses 305 can be formed from an electrically non-conductive, or insulating, material, such as a plastic, a glass, and/or a ceramic, for example, and can include a treatment, such as polytetrafluoroethylene, a lubricant, or some other treatment, to substantially prevent tissue from sticking to the first and second jaws 202, 204 during use.

The first and second jaws 202, 204 can each also include one or more energy delivery surfaces or structures coupled thereto or formed thereon. For example, the first jaw 202 can include one or more electrodes 306 or other energy delivery surfaces or structures formed thereon, and the second jaw 204 can include one or more electrodes 308 or other energy delivery surfaces or structures formed thereon. The electrodes 306, 308 can be configured to contact issue disposed between the first and second jaws 202, 204 such that energy can be passed between the electrodes 306, 308 through the tissue, thereby causing resistive heating of the tissue.

The electrodes 306, 308 can be in communication with an electrical source (not shown) via one or more conductors 702 (see FIG. 7) that can extend along a length of the shaft 108. In one embodiment, the electrical source can be operable to deliver radio frequency (RF) or other electrical energy to the electrode 306 at a first polarity and to the electrode 308 at a second (opposite) polarity, such that RF current can flow between the electrodes 306, 308 and thereby through tissue captured between the first and second jaws 202, 204. In some embodiments, the actuating beam 206 can serve as an electrical conductor that can cooperate with the electrodes 306, 308 (e.g., as a ground return) for delivery of bipolar RF energy to tissue captured between the first and second jaws 202, 204. The electrical source can be external to the instrument 100 or can be integral therewith (e.g., in the proximal actuating portion 104, etc.). A controller (not shown) can regulate delivery of power from the electrical source to the electrodes 306, 308. The controller can also be external to the instrument 100 or can be integral therewith (e.g., in the proximal actuating portion 104, etc.). The electrodes 306, 308 are shown as single, continuous electrodes that extend around a periphery of each of the first and second jaws 202, 204, respectively. In other embodiments, however, the electrodes can be provided in a variety of alternative locations, configurations, and relationships.

In some embodiments, the end effector 102 can include one or more sensors (not shown) that can be configured to sense a variety of parameters at the end effector 102, including but not limited to temperature of adjacent tissue, electrical resistance or impedance of adjacent tissue, voltage across adjacent tissue, force exerted on the first and second jaws 202, 204 by adjacent tissue, etc. By way of example only, the end effector 102 can include one or more positive temperature coefficient (PTC) thermistor bodies (e.g., PTC polymer, etc.; not shown) located adjacent to the electrodes 306, 308 and/or elsewhere. During use, data from sensors may be communicated to the controller (not shown) and can be processed by the controller in a variety of ways. By way of example only, the controller can modulate or otherwise change the RF energy being delivered to the electrodes 306, 308 based at least in part on data acquired from one or more sensors at the end effector 102. In addition or alternatively, the controller can alert the user to one or more conditions via an audio, visual, and/or haptic feedback device (e.g., a speaker, lights, a display screen, a vibrating element, etc.) based at least in part on data acquired from one or more sensors at the end effector 102. Certain types of sensors need not necessarily be in communication with the controller and can simply provide a localized effect at the end effector 102. For instance, PTC thermistor bodies (not shown) at the end effector 102 can automatically reduce the amount of energy delivery at the electrodes 306, 308 as the temperature of the tissue and/or the end effector 102 increases, thereby reducing the likelihood of overheating. In some embodiments, a PTC thermistor element (not shown) can be in series with the power source (not shown) and the electrodes 306, 308 and the PTC thermistor can provide an increased impedance (reducing flow of current) in response to temperatures exceeding a threshold. Furthermore, the electrodes 306, 308 can be used as sensors (e.g., to sense tissue impedance, etc.). Any of a variety of other sensors can be incorporated into the instrument 100 and data from such sensors can be utilized in a variety of different manners by the controller or otherwise.

As discussed, for example, in U.S. Pat. Pub. Nos. 2012/0078139 and 2012/0078247, the entire contents of which are incorporated by reference herein, RF energy is a form of electrical energy that can be in the frequency range of 300 kHz to 1 MHz. The instrument 100 can be configured to transmit low frequency RF energy through tissue, which can cause ionic agitation, or friction, in effect resistive heating, thereby increasing the temperature of the tissue. Because a sharp boundary can be created between treated tissue and surrounding tissue, users of the instrument 100, e.g., surgeons and/or other medical professionals, can operate on the tissue with a high level of precision and control without damaging un-targeted adjacent tissue. The low operating temperatures of RF energy can be useful for removing, shrinking, or sculpting soft tissue while simultaneously sealing blood vessels. RF energy can work particularly well on connective tissue, which is primarily comprised of collagen and shrinks when contacted by heat. Heat generated by current flow from the RF energy through tissue to which the RF energy is applied can seal the tissue, e.g., form hemostatic seals within the tissue and/or between tissues, and can thus be particularly useful for sealing blood vessels, for example. When the instrument 100 includes a cutting element configured to cut tissue clamped between the jaws and is configured to apply energy to tissue clamped between the jaws so as to seal the tissue, the instrument 100 can be configured to separately cut and seal tissue clamped between the jaws or can be configured to simultaneously cut and seal tissue clamped between the jaws.

Figure 4:
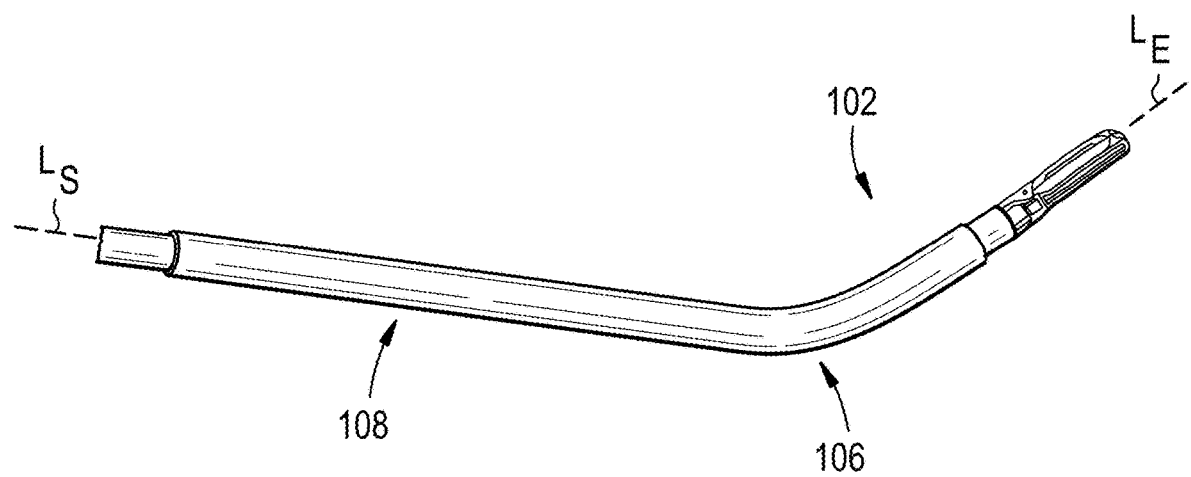
FIG. 4 is a top view of the surgical instrument of FIG. 1 in an articulated configuration.

As noted above, the instrument 100 can include an articulating portion 106, which can be operable to selectively position the end effector 102 at various angles relative to the longitudinal axis $L_I$ defined that passes through the shaft 108. FIG. 4, for example, illustrates the instrument 100 in an articulated configuration in which the end effector 102 is positioned such that a longitudinal axis $L_E$ thereof is transverse to a longitudinal axis $L_S$ of the shaft 108. Such a configuration can be contrasted to the neutral, centered, or "home" configuration of FIGS. 1 and 2, wherein the end effector longitudinal axis $L_E$ and shaft longitudinal axis $L_S$ are collinear, as indicated by the longitudinal axis $L_I$ in FIG. 1.

Figure 5:
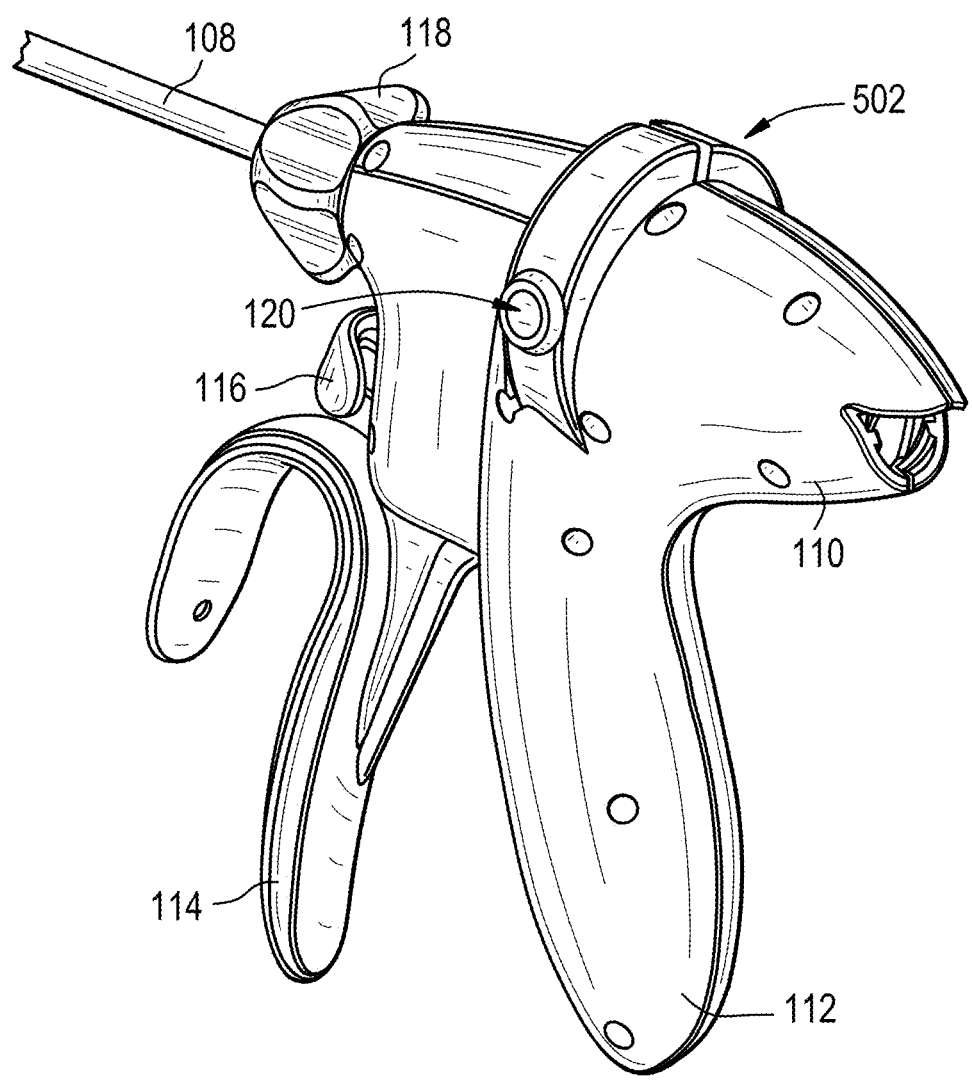
FIG. 5 is a perspective detail view of a proximal portion of the surgical instrument of FIG. 1.

The instrument 100 can be configured for "passive" articulation, in which external force from an immovable object is utilized to articulate the end effector 102 relative to the shaft 108 and proximal actuating portion 104. For example, in some embodiments a surgeon or other user can press the end effector 102 against a portion of a patient's anatomy during a procedure to effect articulation of the end effector. In other embodiments, the end effector can be pressed against another instrument present at the surgical site. In some embodiments, the instrument 100 can include a mechanism to selectively permit or prevent articulation of the end effector 102 relative to the shaft 108 and/or proximal actuating portion 104. In one embodiment, an articulation control 120 can be utilized by a surgeon or other user to selectively lock and/or unlock movement of the articulating portion 106. The articulation control 120 can have a number of configurations and, in one embodiment, can be a button that can be depressed by a surgeon or other user to permit articulation. As shown in FIG. 5, articulating movement of the end effector 102 can be permitted by depressing the button control 120 toward a stationary base 502. In some embodiments, the button control 120 can be biased outward away from the stationary base 502 such that the instrument 100 is biased to a locked configuration in which articulation is prevented. Still further, and as noted above, in some embodiments the end effector 102 can also be biased toward a neutral or centered position in which the longitudinal axis $L_E$ and the longitudinal axis $L_S$ are collinear and/or parallel, such that the end effector can be returned to this neutral position by depressing the button control 120 without pressing the end effector 102 against any external structure.

Passive articulating electrosurgical instruments, such as the instrument 100, can face a unique disadvantage resulting from the need to press the end effector 102 against an external structure to effect articulation of the instrument: unintended damage to the external structure. As noted above, electrosurgical instruments pass RF or other electrical energy through tissue disposed between the first and second jaws 202, 204 to selectively heat the tissue. The delivery of electrical energy that generates heat in the tissue, however, also generates heat in the end effector 102 itself. This is because the first and second jaws 202, 204 and/or other structures of the end effector 102 are typically formed from materials that are good thermal conductors, e.g., metals. As a result, the end effector 102 can reach an elevated temperature during use that is high enough to cause damage upon contact with tissue. Moreover, the end effector 102 can often remain at such an elevated temperature for some time after electrical energy delivery ends. Accordingly, external surfaces of the end effector 102 can damage tissue as the end effector is pressed against an anatomic structure to effect passive articulation during a surgical procedure. This can require a surgeon or other user to insert a second instrument to serve as the object against which the end effector is pressed to effect articulation. This can introduce a number of additional problems and/or complications, including the need to use an instrument that can withstand contact with the elevated temperature end effector, as well as the requirement that a surgeon devote one of his or her hands (or a hand of another surgeon or user) to operating the other instrument. This increases the complexity and cost of the procedure.

Figure 6:
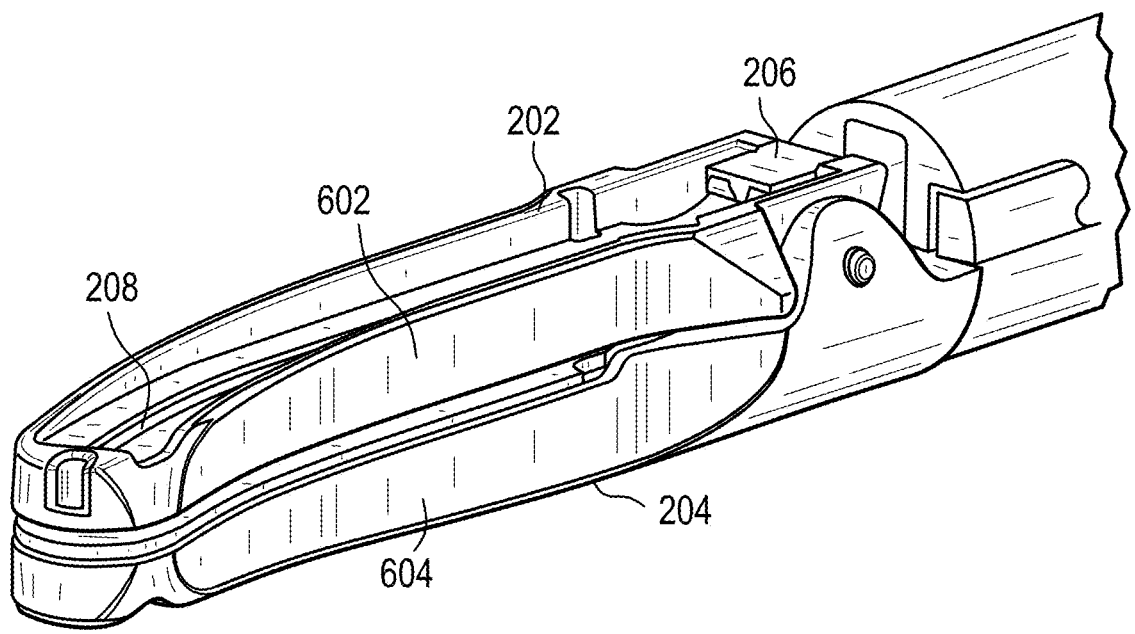
FIG. 6 is a perspective detail view of an end effector of the surgical instrument of FIG. 1.

To address these problems and prevent unintended damage to adjacent tissue during passive articulation maneuvers, the end effector 102 of the instrument 100 can include a thermally insulating (isolative) protective coating formed over external surfaces thereof. As shown in FIG. 6, the first jaw 202 can include a coating 602 formed over its external-facing surfaces, e.g., its side, end, and top surfaces, or all surfaces except those that face the second jaw 204 and are configured to contact tissue disposed between the first and second jaws 202, 204. Similarly, the second jaw 204 can include a coating 604 formed over its external-facing surfaces, e.g., its side, end, and bottom surfaces, or all surfaces except those that face the first jaw 202 and are configured to contact tissue disposed between the first and second jaws 202, 204.

A variety of materials can be utilized for the thermally insulating (isolative) protective coating. For example, a number of polymers can be utilized due to their low thermal conductivity and ability to remain in contact with the elevated-temperature first and second jaws 202, 204 for extended periods of time without degrading, melting, etc. For example, in some embodiments the coating can be formed from a polymer, such as a high-temperature polyamide (e.g., Thermec N™, a glass-filled nylon). In other embodiments, alternative materials can be utilized, such as alumina compounds, yttria-stabilized zirconia (YSZ), or poly-para-xylylene polymers, such as Parylene™.

Moreover, a variety of different material thicknesses can be utilized, depending upon the effectiveness (e.g., the thermal conductivity) of the material selected for the thermally insulating coating, the temperatures to which the end effector components are raised, and the desired maximum temperature of an external surface of the protective coating. In some embodiments, for example, the thermally insulating material can have a thickness between about 0.15 mm and about 1 mm.

The thermally insulating material can be coupled to the outward-facing surfaces of the end effector 102 in a variety of manners. For example, in some embodiments a thermally insulating material can be applied by plasma or spray treatment onto the outward-facing surface of at least one of the first and second jaws 202, 204. In other embodiments, a chemical or physical vapor deposition process can be utilized. In other embodiments, a molding process can be utilized to cover outward-facing surfaces of the end effector 102 with the thermally insulating material. For example, in some embodiments the thermally insulating material can be insert molded or over-molded onto at least one of the first and second jaws 202, 204. In still other embodiments, insulating material can be vacuum formed over end effector 102 or the end effector can be masked and dipped into liquid insulating material that can dry to form a coating over an outer surface thereof.

The combination of a thermally insulating or isolating coating formed over outward-facing surfaces of an end effector configured to deliver electrical energy to tissue for cutting and/or sealing can address the unique problem of collateral tissue damage encountered when such an instrument is configured for passive articulation. Addressing the problem in the manner described herein can maintain the suitability of passive articulation for this type of instrument, which can be advantageous because passive articulating instruments can be less complex, less expensive, and smaller than counterpart instruments that include components to effect active articulation. Moreover, by eliminating unintended damage to adjacent tissue during passive articulating maneuvers, single-handed articulation can be enabled because a user will not need to operate a second instrument to exert an external force on the end effector in place of adjacent tissue when the end effector is known to be at an elevated temperature that can cause damage upon contact.

Figure 7:
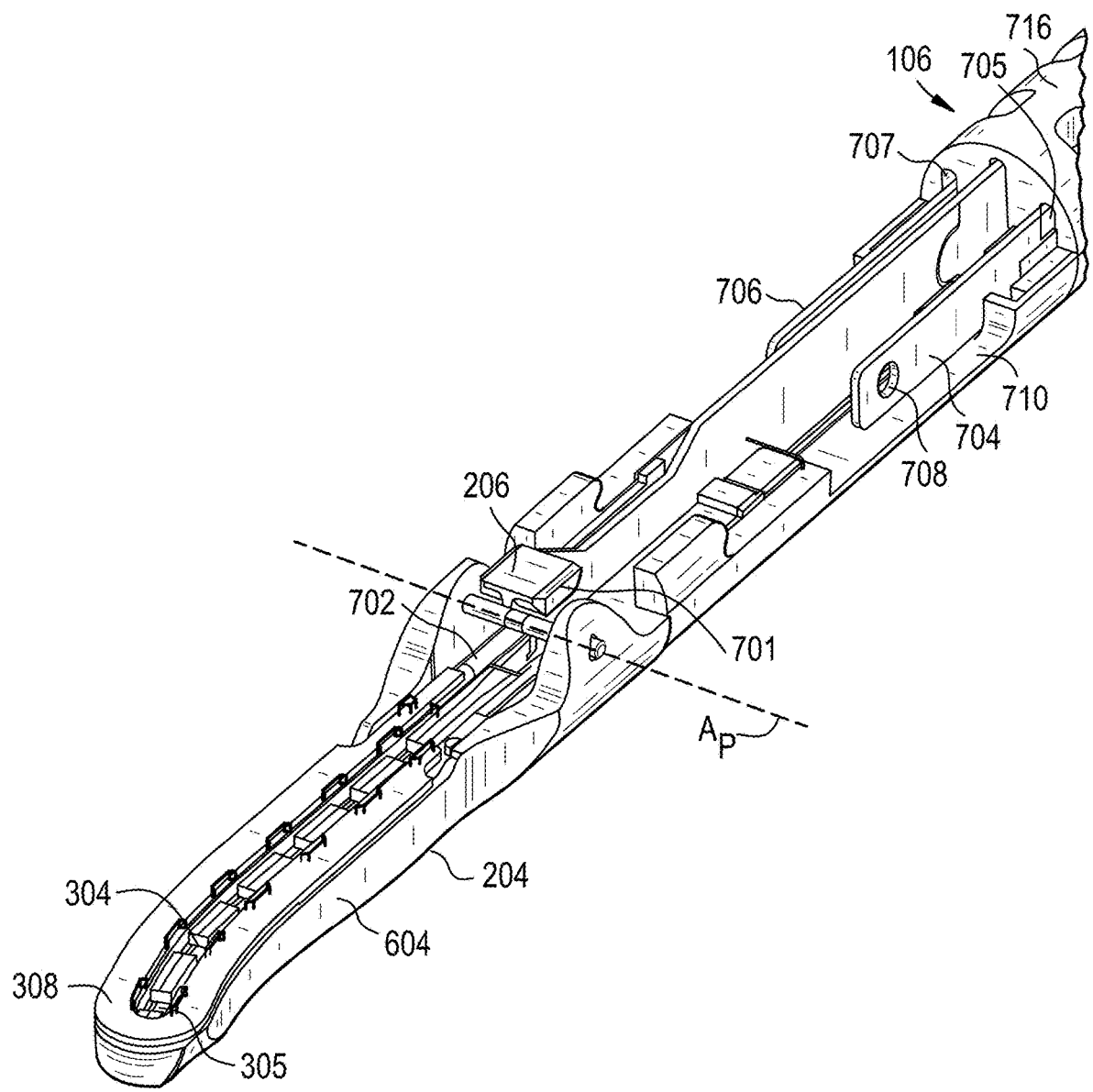
FIG. 7 is a perspective partial cut-away view of a distal portion of the surgical instrument of FIG. 1.
Figure 8:
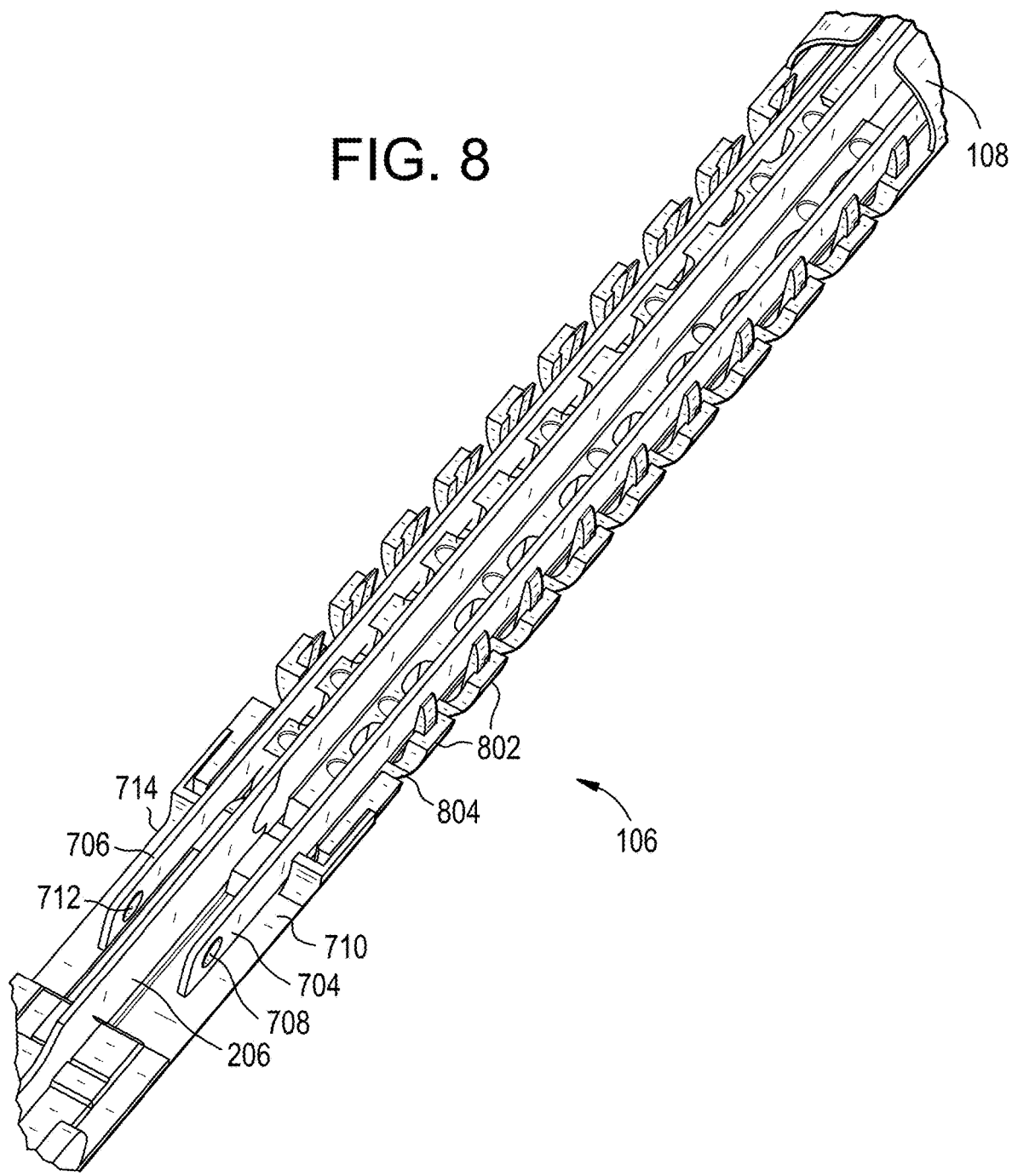
FIG. 8 is a perspective partial cut-away view of an articulating portion of the surgical instrument of FIG. 1.

FIGS. 7 and 8 illustrate portions of the end effector 102 and articulating portion 106 in more detail. As shown in the figures, the instrument 100 can include articulation control bands 704, 706 that extend through the articulating portion 106 and shaft 108 along with other components, such as the actuating beam 206 and energy delivery conductor 702. The articulation control bands 704, 706 can be constrained against movement other than axial translation by lumens 705, 707 formed in the articulation portion 106 and the shaft 108. The articulation control bands can be coupled to the end effector 102 in a variety of manners. In the illustrated embodiment, the articulation control bands 704, 706 terminate near a proximal end of the end effector 102. Each articulation control band can include a through-hole 708, 712 that can be used to receive a bolt, rod, or other coupling member (not shown). The coupling member for each articulation control band 704, 706 can be sized to fit within a slot 710, 714 formed in a sidewall of the end effector 102 to anchor a distal end of each articulation control band to the end effector. In other embodiments, however, alternative coupling methods can be employed. For example, the articulation control bands 704, 706 can be bolted, riveted, or laser welded to a proximal end of second jaw 204. The articulation control bands 704, 706 can be coupled to the end effector 102 in any manner that allows a push-pull operation as the end effector is articulated relative to other parts of the instrument 100. That is, the articulation control bands 704, 706 operate such that articulation of the end effector causes one band to be pulled (e.g., advanced distally) while the other is pushed (e.g., retracted proximally). This push-pull actuation causes the articulating portion 106 to bend and change an angle of the end effector 102 relative to the shaft 108, moving it from an orientation in which it is aligned with shaft to a position where the end effector is at an angle to the shaft that can vary from about 1 degree to about 90 degrees, depending on how far the articulation control bands 704, 706 are displaced.

The articulating portion 106 can be configured to elastically deform in one or more directions to allow the end effector 102 to move relative to other components, such as the shaft 108 and the proximal actuating portion 104, that are disposed on an opposite side of the actuating portion. A number of different actuating portion configurations can be utilized. In the illustrated embodiment, the articulating portion 106 can be formed from one or more segments 802 (see FIG. 8) having one or more relief slits 804 formed therein to facilitate bending or other deformation of the articulating portion 106. The relief slits 804 can be formed to facilitate bending or deformation in one direction while resisting the same in other directions. For example, the relief slits 804 formed in the illustrated articulating portion 106 can facilitate lateral bending or deformation in the plane defined by the longitudinal axis $L_I$ and the pivot axis $A_p$, but can resist bending or deformation in other directions due to a solid spine 716 (see FIG. 7) connecting adjacent segments 802 along top and bottom surfaces of the articulating portion. The articulating portion 106 can be formed from a variety of materials and, in some embodiments, can be formed from a thermoplastic, such as, but not limited to, polycarbonate, nylon, polyetherimide, or polyetherketone.

As noted above, an interior of the articulating portion 106 can include a number of lumens formed therein that can be configured to receive various components extending from the end effector 102 toward the proximal actuating portion 104, such as the actuating beam 206 and articulation control bands 704, 706. Additional lumens (not shown) can also be included, e.g., a lumen to carry the energy delivery conductor 702, etc.

Figure 9:
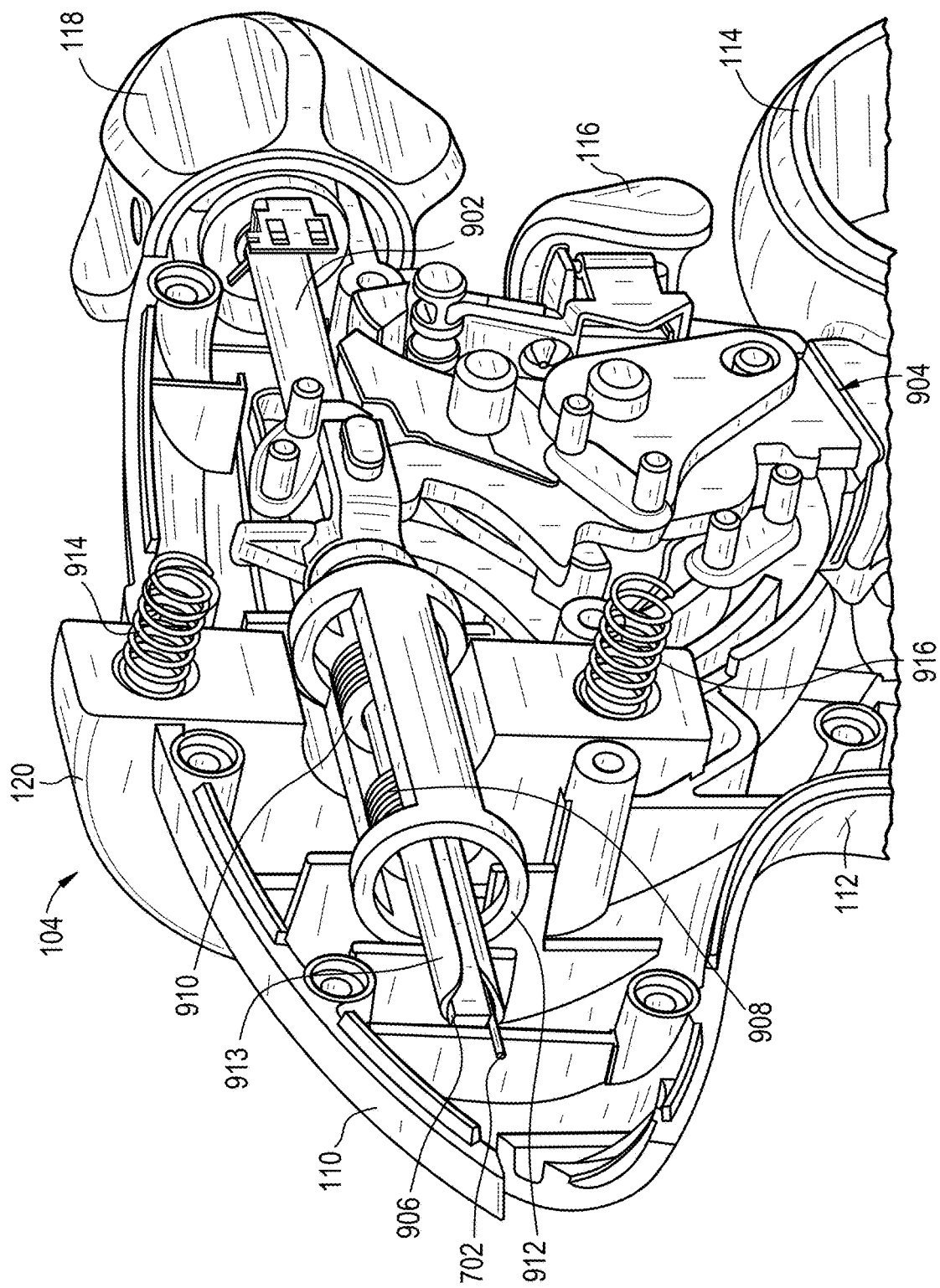
FIG. 9 is a perspective partial cut-away view of a proximal portion of the surgical instrument of FIG. 1.
Figure 10:
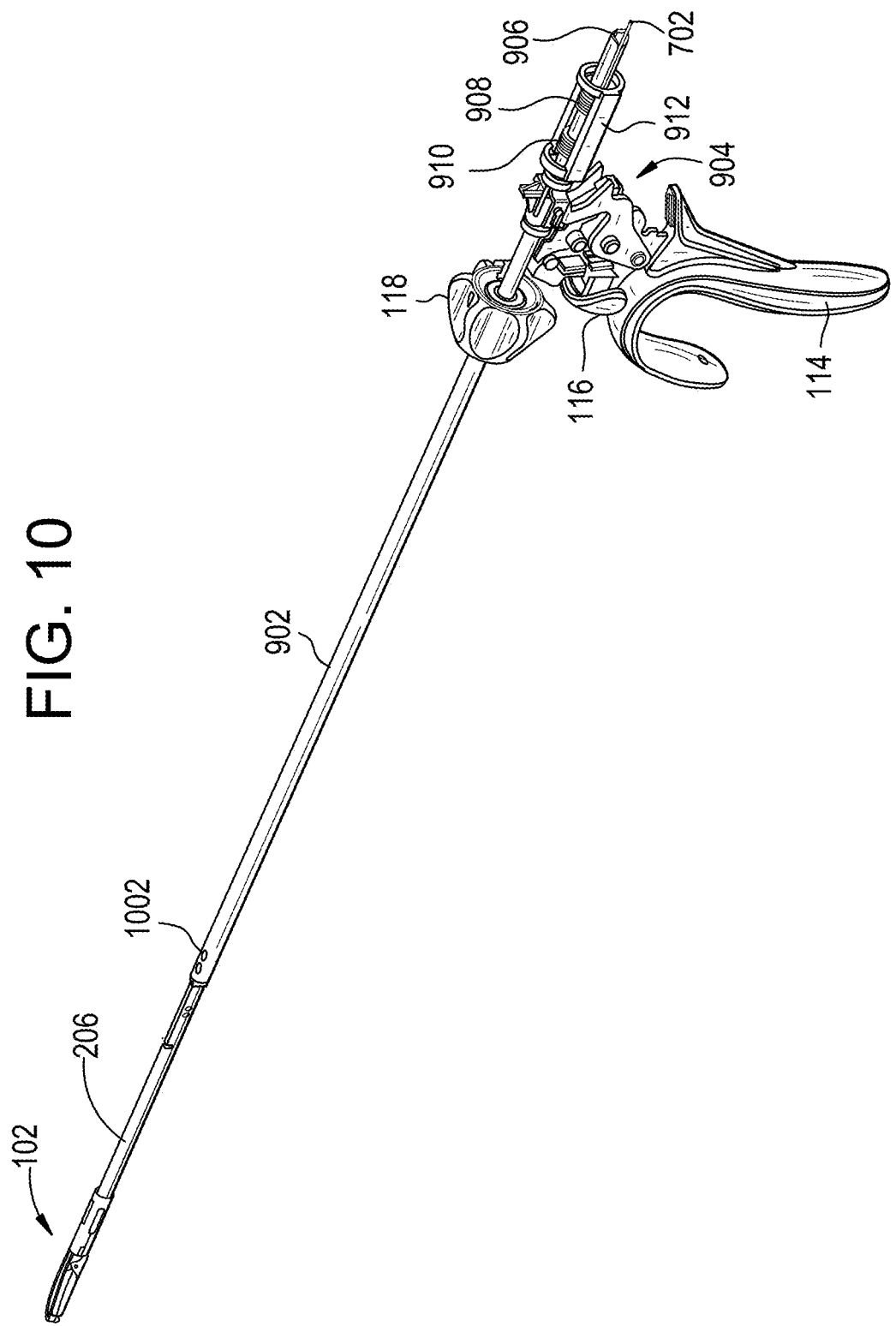
FIG. 10 is an alternative perspective partial cut-away view of a proximal portion of the surgical instrument of FIG. 1.

FIGS. 9 and 10 illustrate the proximal actuating portion 104 in greater detail. As shown in the figures, the rotation control 118 can be positioned at a distal end of the proximal actuating portion 104. The rotation control 118 can take the form of a knob in some embodiments, and can be configured to rotate the end effector 102 about the longitudinal axis $L_E$ thereof. In some embodiments, the rotation control 118 can provide rotation of the end effector 102, the articulating portion 106, and the shaft 108 unitarily. In other embodiments, the knob or other rotation control 118 can be operable to rotate the end effector 102 without rotating any portion of the shaft 108 that is proximal to the articulating portion 106. As another merely illustrative example, the instrument 100 can also include multiple rotation controls, such as a first rotation control that controls rotation of the shaft 108 and the end effector 102 as a single unit, as well as another rotation control that controls rotation of the end effector 102 without rotating any portion of the shaft 108 that is proximal to the articulating portion 106. Other suitable configurations for enabling rotation will be apparent to those of ordinary skill in the art in view of the teachings herein. Of course, rotation features can be omitted in some embodiments.

Extending proximally through the rotation control 118 can be an actuating shaft 902 that can be coupled to the actuating beam 206 at a position 1002 (see FIG. 10) proximal to the articulating portion 106. The actuating shaft 902 can be configured to translate proximally and distally relative to the end effector 102, articulating portion 106, and shaft 108 to effect proximal and distal translation of the actuating beam 206 in response to movement of the first trigger 114. A linkage 904 can transfer motion of the first trigger 114 to translation of the actuating shaft 902.

A track 906 can be disposed within an inner lumen of the actuating shaft 902 and can serve as a support for the articulation control bands 704, 706 extending from the proximal actuating portion 104 to the articulating portion 106. The track 906 can also provide a lumen for routing the energy delivery conductor 702 through the shaft 108. In the proximal actuating portion 104, the energy delivery conductor 702 can be coupled to the above-described controller (not shown), power source (not shown), and second trigger 116 to allow selective delivery of RF or other electrical energy to tissue via the electrodes or other energy delivery structures or surfaces 306, 308.

The articulation control bands 704, 706 that extend along the track 906 can be coupled at a proximal end thereof to a locking element that interfaces with an articulation locking actuator to selectively permit translation of the articulation control bands relative to the housing 110 of the proximal actuating portion 104. In the illustrated embodiment, the first articulation control band 704 can be coupled to a first locking element 908 and the second articulation control band 706 can be coupled to a second locking element 910. Each of the locking elements 908, 910 can be in the form of a ring slidingly disposed about the actuating shaft 902 that has splines or threads formed on an outer surface thereof. The actuating shaft 902 can include opposed slots 913 formed therein that can allow for coupling the articulation control bands 704, 706 to the locking elements 908, 910, respectively. An articulation locking actuator 912 can be coupled to the articulation control 120, can have a cylindrical shape positioned to encircle the locking elements 908, 910. The articulation locking actuator 912 can include a portion having complementary splines or threads formed thereon that can selectively interface with the splines or threads of the first and second locking elements 908, 910 to prevent proximal and/or distal translation thereof. By virtue of its coupling to the articulation control 120, the articulation locking actuator 912 can be configured such that the biasing force of the springs 914, 916 presses the locking elements 908, 910 and articulation locking actuator 912 together. And conversely, depression of the articulation control 120 against the biasing force of the springs 914, 916 can move the articulation locking actuator 912 out of contact with the first and second locking elements 908, 910, thereby permitting translation of the first and second articulation control bands 704, 706.

Figure 11:
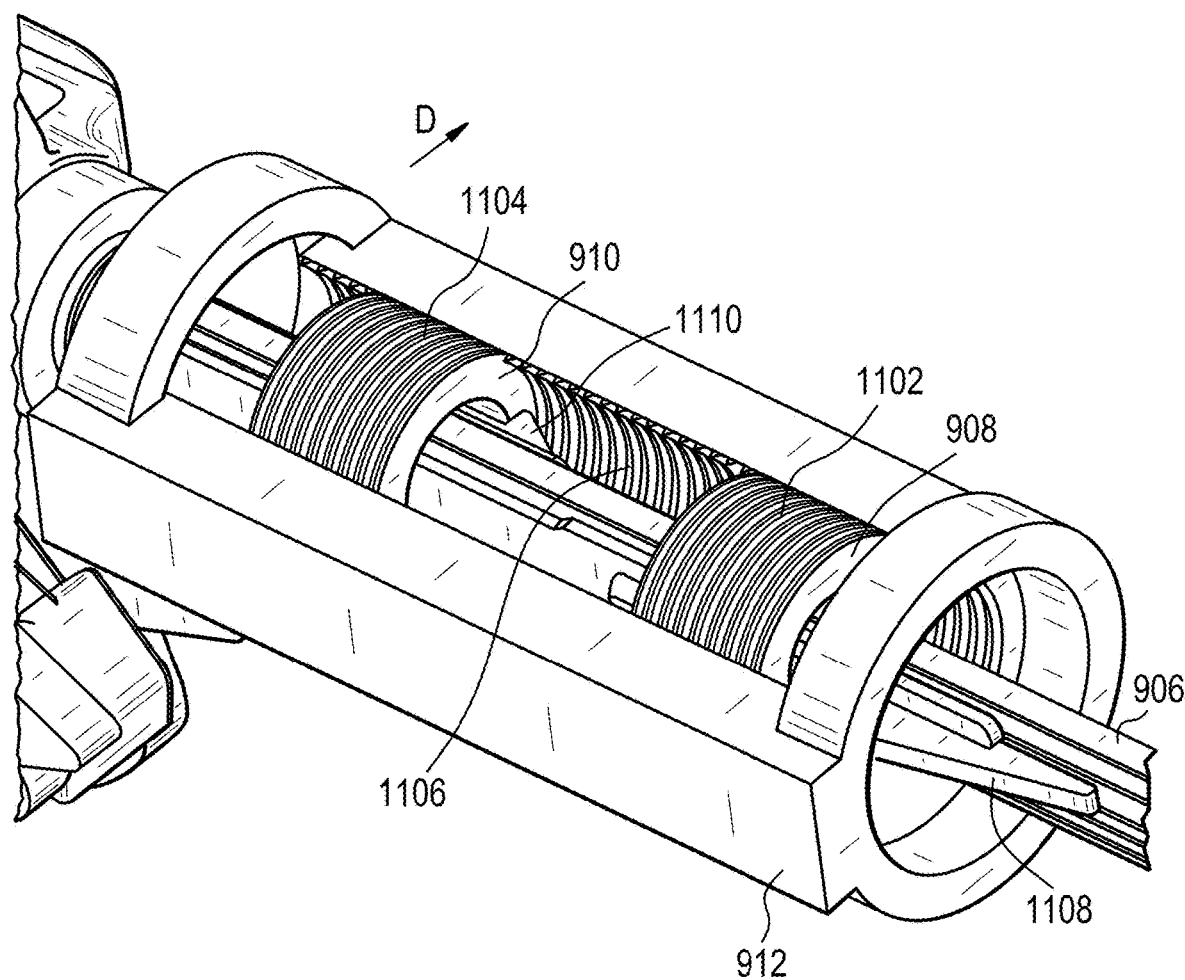
FIG. 11 is a perspective detail view of an articulation locking actuator and articulation locking elements of the surgical instrument of FIG. 1.

FIGS. 11-17 illustrate alternative views of the first and second locking elements 908, 910 and the articulation locking actuator 912. FIG. 11 illustrates the articulation locking actuator 912 in a configuration wherein splines or threads 1106 formed on an internal surface thereof are interfaced with splines or threads 1102 of the first locking element 908 and splines or threads 1104 of the second locking element 910. In such a configuration, the articulation locking actuator 912, which is constrained from moving proximally or distally relative to the housing 110 of the proximal actuating portion 104, prevents the locking elements 908, 910 from translating proximally or distally relative to the track 906. Moreover, because a protrusion 1108 at a proximal end of the first articulation control band 704 is coupled to the first locking element 908 and a protrusion 1110 at a proximal end of the second articulation control band 706 is coupled to the second locking element 910, the articulation control bands 704, 706 are also prevented from translating proximally and/or distally relative to the track 906. Locking the articulation control bands 704, 706 in this manner can effectively lock the position and/or orientation of the end effector 102 relative to the remainder of the instrument 100, including the proximal actuating portion 104 and the shaft 108.

Figure 12:
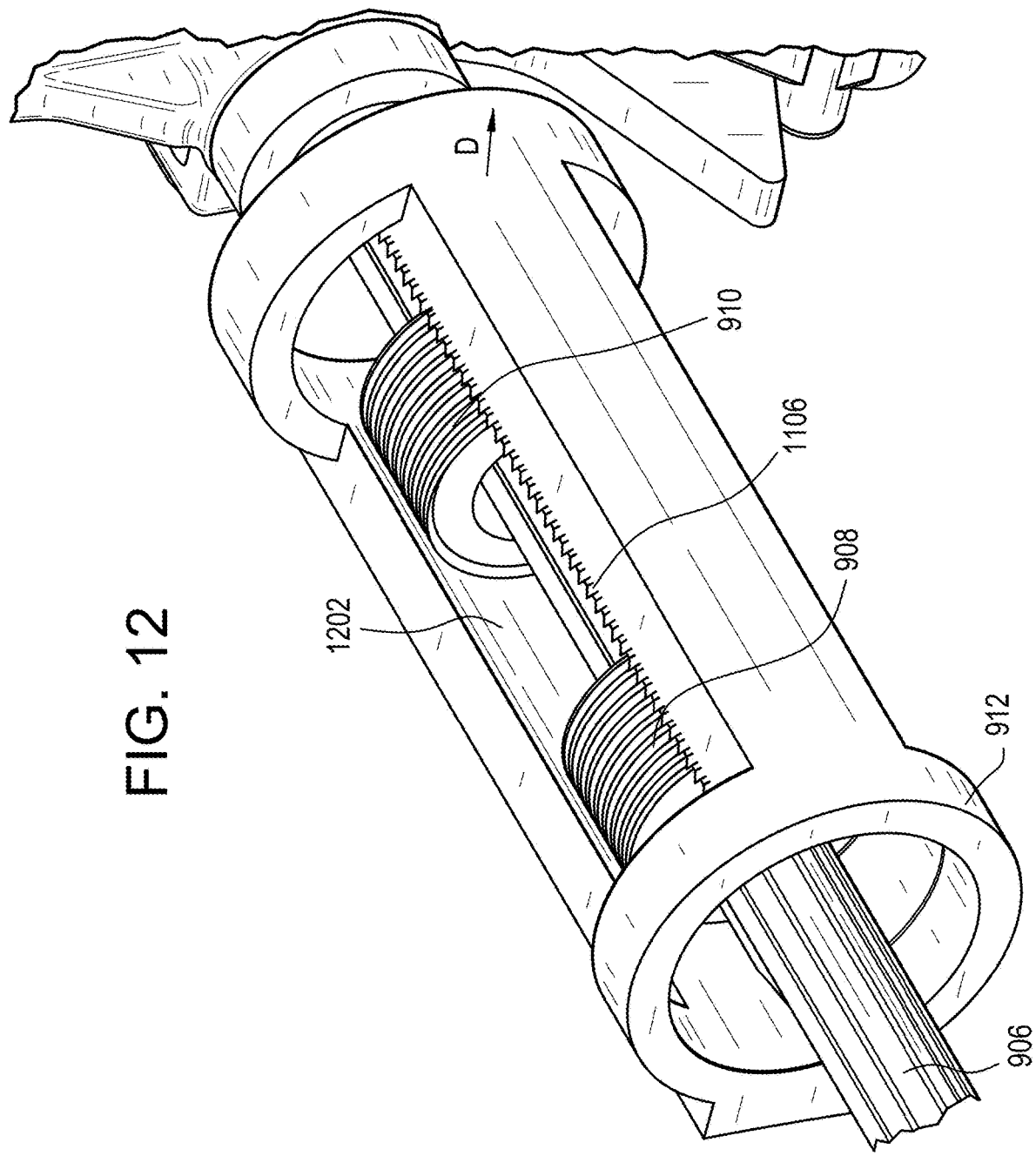
FIG. 12 is an alternative perspective detail view of the articulation locking actuator and articulation locking elements of the surgical instrument of FIG. 1.

FIG. 12 illustrates the components of FIG. 11 from an opposite perspective. In this view it can be seen that the articulation locking actuator 912 includes a surface 1202 opposite the splines or threads 1106 that is smooth. Further, there is clearance between the surface 1202 and the first and second locking elements 908, 910. Such an arrangement can allow the articulation locking actuator 912 to move in the direction of arrow D when a user depresses the articulation control 120 to free the splines 1106 from those of the first and second locking elements 908, 910, thereby permitting proximal and/or distal translation of the articulation control bands 704, 706 and the accompanying articulation of the end effector 102.

Figure 13:
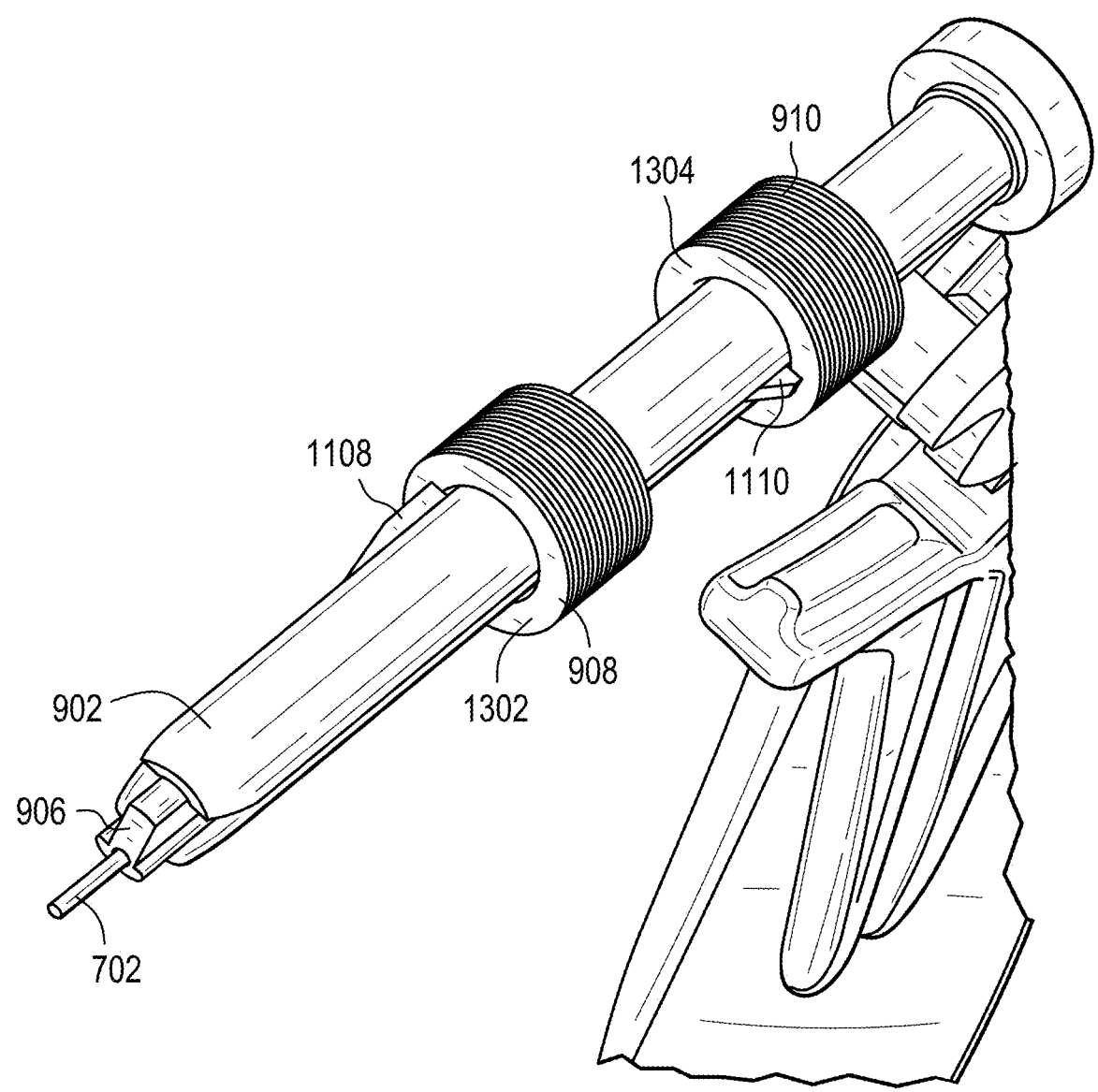
FIG. 13 is a perspective detail view of the articulation locking elements of the surgical instrument of FIG. 1.
Figure 14:
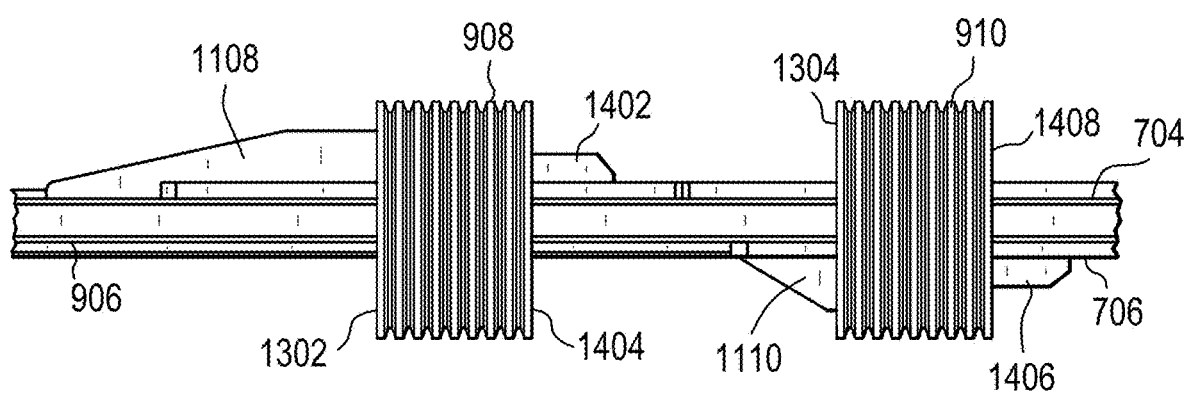
FIG. 14 is a top detail view of the articulation locking elements of the surgical instrument of FIG. 1.

FIGS. 13 and 14 illustrate the first and second locking elements 908, 910 and their coupling to the first and second articulation bands 704, 706 in more detail. As noted above, each locking element 908, 910 can be in the form of a ring disposed about the actuating shaft 902 and configured to slidably move relative thereto. As a result, the actuating shaft 902 can be advanced distally or retracted proximally to, e.g., actuate the first and second jaws 202, 204 of the end effector 102 without causing movement of the articulation control bands 704, 706. Each locking element 908, 910 can include a proximal face 1302, 1304, respectively, that can abut against protrusions 1108, 1110 formed at proximal ends of the articulation control bands 704, 706. The protrusions 1108, 1110 formed at the proximal ends of the articulation control bands 704, 706 can extend through the slots 913 formed in the actuating shaft 902 to prevent interference when these components translate axially relative to one another.

The top view of FIG. 14 illustrates in more detail the coupling of each locking element 908, 910 to each articulation control band 704, 706, respectively. As shown in the figure, the protrusion 1108 formed at the proximal end of the articulation control band 704 can extend beyond an inner diameter of the locking element 908 such that a portion of the protrusion abuts against a proximal-facing surface 1302 of the locking element 908. This can prevent the articulation control band 704 from advancing distally when the locking element 908 is constrained against proximal/distal movement by the articulation locking actuator 912. Moreover, the protrusion 1108 can include a distal portion 1402 that extends distally beyond a distal-facing surface 1404 of the locking element 908. The distal portion 1402 can extend substantially to an inner diameter of the locking element 908 to form an interference fit therewith, such that the locking element 908 is fixed relative to the articulation control band 704 when moved both proximally and distally. Further, a distal-most end of the distal portion 1402 can be tapered to facilitate assembly. Similarly, a protrusion 1110 formed at a proximal end of the articulation control band 706 can be sized to abut against a portion of a proximal-facing surface 1304 of the locking element 910. And the protrusion 1110 can include a distal portion 1406 that can extend through the locking element 910 beyond a distal-facing surface 1408 thereof.

Figure 15:
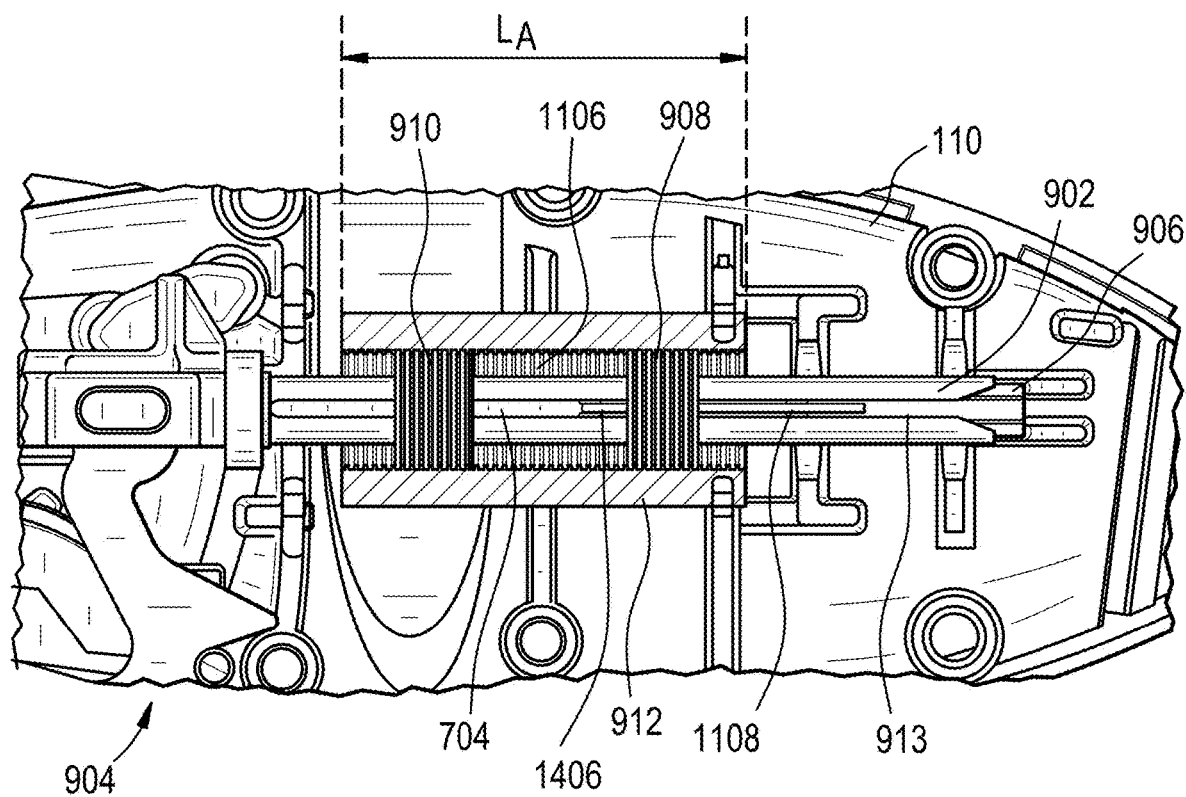
FIG. 15 is a side partial cut-away view of a proximal portion of the surgical instrument of FIG. 1.

The side view of FIG. 15 illustrates the interaction of the actuating shaft 902, articulation control band 704, locking element 908, and articulation locking actuator 912. For example, the figure shows the protrusion 1108 extending through the slot 913 of the actuating shaft 902. In addition, a length LA of the articulation locking actuator 912 having threads or splines 1106 formed thereon shows a range of motion available to the locking elements 908, 910 (and therefore articulation control bands 704, 706) during articulating maneuvers.

Figure 16:
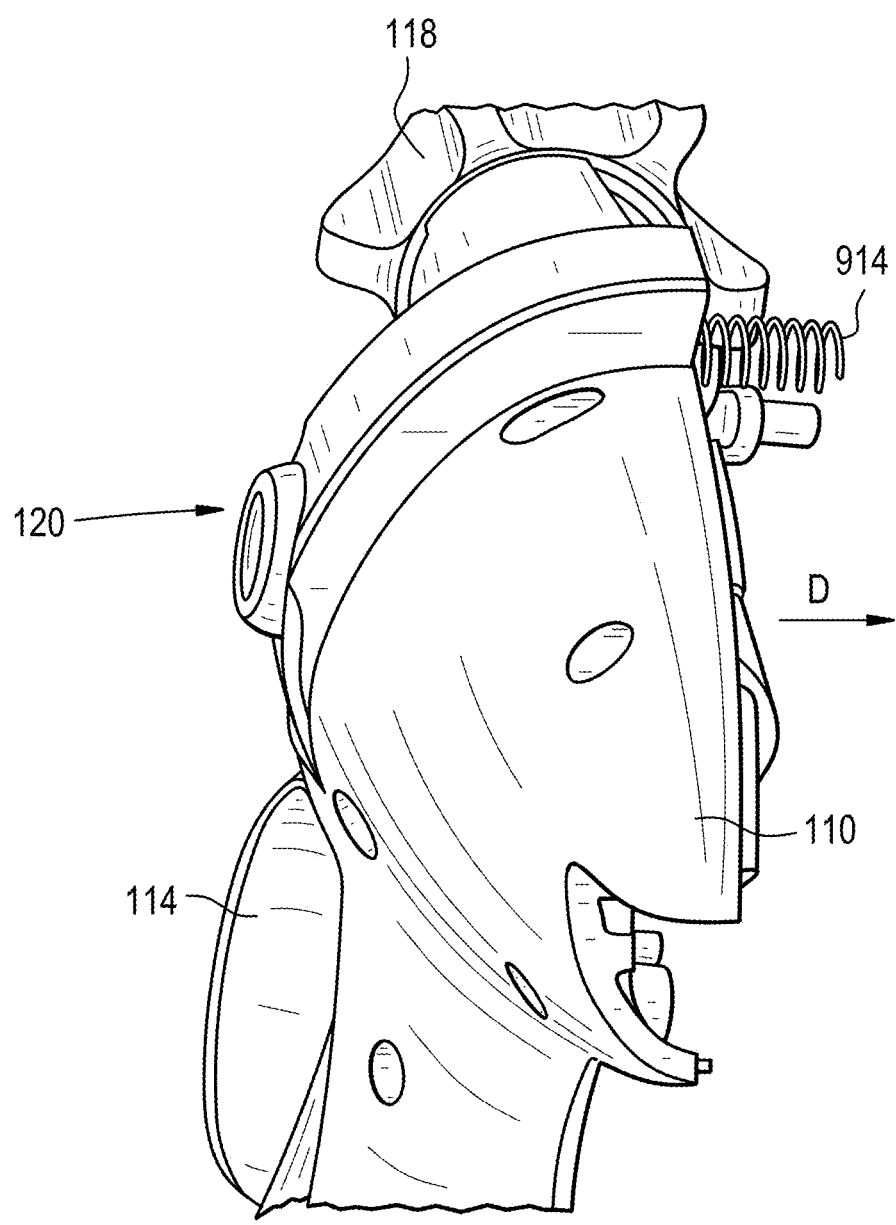
FIG. 16 is a perspective partial cut-away view of a proximal portion of the surgical instrument of FIG. 1.
Figure 17:
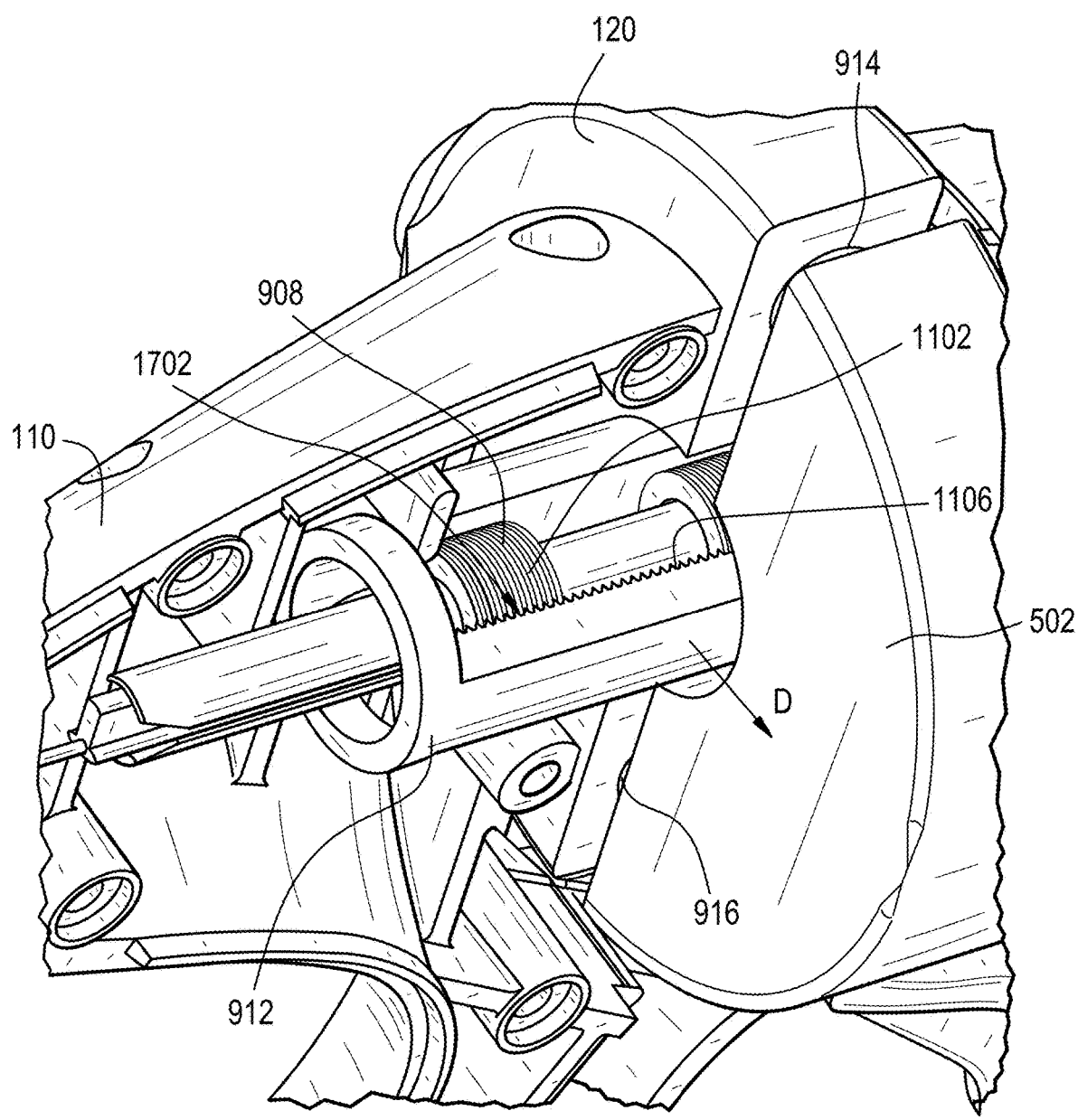
FIG. 17 is an alternative perspective partial cut-away view of the surgical instrument of FIG. 1.

FIGS. 16 and 17 illustrate alternative views of component interaction when a surgeon or other user depresses the articulation control 120 to selectively permit or prevent articulation of the end effector 102. As noted above, the illustrated embodiment is an instrument 100 biased to a locked configuration wherein articulation is prevented by the biasing force of springs 914 and 916 that urge the articulation control 120 away from the stationary portion 502. Due to the coupling of the articulation control 120 and the articulation locking actuator 912, the biasing force of the springs 914, 916 also urges the articulation locking actuator away from the stationary portion 502, which causes the splines 1106 thereon to interface with the splines 1102, 1104 of the locking elements 908, 910, respectively, to prevent proximal/distal translation thereof.

When a surgeon or other user depresses the articulation control 120 toward the stationary base 502 against the biasing force of the springs 914, 916, the articulation locking actuator 912 is moved in the same direction, as shown by the arrow D. Laterally shifting the articulation locking actuator 912 in this manner can cause separation of the splines 1106 from the splines 1102 of the locking element 908, as shown by arrow 1702 in FIG. 17, which can free the locking element 908 and articulation control band 704 to translate proximally or distally. While not as visible in the figure, the locking element 910 and articulation band 706 are freed by this same movement of the articulation locking actuator 912. Articulation can then be performed by pressing an insulated outer surface of the end effector 102 against a portion of a patient's anatomy. Urging the end effector 102 laterally to one side, for example, will cause the opposed articulation control band to be advance distally. After articulation is complete, a surgeon or other user can release the articulation control 120. This can cause the articulation locking actuator 912 to move opposite the arrow D away from the stationary base 502 such that its splines 1106 reengage with splines 1102 of the locking element 908 (and splines 1104 of the locking element 910) to constrain the locking elements, and articulation bands 704, 706 coupled thereto, from further movement proximally or distally. This can effectively lock the then-existing orientation of the end effector until the user again depresses the articulation control 120.

While the above description highlights features of the illustrated embodiment of an electrosurgical instrument, surgical methods are also considered within the scope of the present disclosure. In an exemplary method, the end effector 102 can be inserted into a patient via a trocar. The articulating portion 106 can be substantially straight when the end effector 102 and part of the shaft 108 are inserted through the trocar. The articulation control 120 can then be actuated to enable pivoting or flexing of the articulating portion 106 in order to position the end effector 102 at a desired position and/or orientation relative to an anatomical structure within the patient. This can be accomplished by a surgeon or other user pressing the end effector 102 against a portion of the patient's anatomy while depressing the articulation control 120. Once a desired position and/or orientation is achieved, the surgeon or other user can release the articulation control 120 to lock the position and/or orientation of the end effector 102. One or more layers of tissue of the anatomical structure can be captured between the first and second jaws 202, 204 by squeezing the first trigger 114 toward the pistol grip 112. In some embodiments, captured layers of tissue can be part of the same natural lumen defining an anatomical structure in a patient (e.g., blood vessel, portion of gastrointestinal tract, portion of reproductive system, etc.). For instance, one tissue layer can include the top portion of a blood vessel while the other tissue layer may include the bottom portion of the blood vessel, along the same region of length of the blood vessel (e.g., such that a fluid path through the blood vessel before use of the electrosurgical instrument 100 is perpendicular to the longitudinal axis $L_E$ defined by the end effector 102, etc.). In other words, the lengths of the first and second jaws 202, 204 can be oriented perpendicular to (or at least generally transverse to) the length of the blood vessel. As noted above, the actuating beam 206 can be advanced to close the first and second jaws 202, 204 by squeezing the first trigger 114 toward the pistol grip 112.

With tissue layers captured between the first and second jaws 202, 204, the actuating beam 206 can continue to advance distally as the user squeezes the first trigger 114 or actuates, e.g., the second trigger 116 or another trigger. As the actuating beam 206 advances further distally, the distal blade of the beam can simultaneously sever the clamped tissue layers, resulting in separated upper layer portions being apposed with respective separated lower layer portions. In some embodiments, this can result in a blood vessel being cut in a direction that is generally transverse to the length of the blood vessel. The flanges of the actuating beam 206 immediately above and below the first and second jaws 202, 204, respectively, can help keep the first and second jaws 202, 204 in a closed and tightly clamped position. With severed tissue layer portions compressed between the first and second jaws 202, 204, the electrode surfaces 306, 308 can be activated to deliver bipolar RF or other electrical energy by the user depressing, e.g., the second trigger 116. In some embodiments, the electrodes 306, 308 can be selectively coupled with a power source (e.g., by the user depressing the second trigger, another button, etc.) such that the electrode surfaces 306, 308 of the first and second jaws 202, 204 can be activated with a common first polarity while the actuating beam 206 is activated at a second polarity that is opposite to the first polarity. Thus, a bipolar RF current can flow between the actuating beam 206 and the electrode surfaces 306, 308 of the first and second jaws 202, 204, through the compressed regions of severed tissue layer portions. In some embodiments, the electrode surface 306 can have one polarity while the electrode surface 308 can have the other polarity with the actuating beam 206 being at one of the polarities or being omitted from the electrical circuit. Regardless of the particular polarity configuration, RF energy delivered by a power source can thermally weld the tissue layer portions on one side of the actuating beam 206 together and the tissue layer portions on the other side of the actuating beam 206 together.

Heat generated by the energy delivery process can denature the collagen within the tissue layer portions and, in cooperation with clamping pressure provided by the first and second jaws 202, 204, the denatured collagen can form a seal within the tissue layer portions. Thus, the severed ends of the natural lumen defining an anatomical structure can be hemostatically sealed shut, such that the severed ends will not leak bodily fluids. In some embodiments, the electrode surfaces 306, 308 can be activated with bipolar RF energy before the actuating beam 206 begins to translate distally and, thus, before the tissue is severed. For instance, such timing can be provided in versions where the second trigger 116 serves to control both tissue sealing and transection, or in embodiments wherein the second trigger 116 serves to mechanically prevent full actuation of the first trigger 114 or another trigger that controls tissue transection unless the second trigger is actuated.

Following tissue sealing and/or transection, the first and second jaws 202, 204 can be opened to free the tissue that was clamped therebetween and the instrument 100 can be repositioned for additional use. In some cases, repositioning the instrument 100 can include articulating the end effector 102 to a new position. Articulation can be performed in the manner described above and, as a result of the insulating coating 602, 604 on the end effector 102, tissue damage to adjacent portions of the patient's anatomy can be avoided even though the elevated temperature end effector is pressed thereagainst during the articulation maneuver. This process can be repeated as often as necessary to complete the surgical procedure.

The instruments disclosed herein can be formed from a variety of materials and can have a variety of different sizes and shapes. For example, instruments or components thereof can be formed from various polymers and/or metals. Furthermore, particular components can be formed from different materials than other components. By way of further example, a proximal actuator portion can be formed from a polymer material, (e.g., polycarbonate), while an end effector can be formed from a metal, such as surgical grade stainless steel (e.g., 17-4), other 300 and 400 series stainless steels, titanium, and aluminum, perhaps to take advantage of greater rigidity. Of course, these are just non-limiting examples of possible material combinations. Instrument sizes can also vary greatly, depending on the intended use and surgical site anatomy.

As noted above, in certain embodiments, the distal end effector 102, articulating portion 106, and shaft 108 can be sized and configured to fit through trocars having various inner diameters, such that the electrosurgical instrument 100 can be used in minimally invasive surgery. Of course, the electrosurgical instrument 100 can also be used in open procedures if desired. By way of example only, with the first and second jaws 202, 204 in a closed position, the end effector 102, articulating portion 106, and shaft 108 can have an outer diameter of about 12 mm in some embodiments. In other embodiments, these components can have an outer diameter of about 5 mm. In still other embodiments, these components can have any other suitable outer diameter (e.g., between approximately 2 mm and approximately 20 mm, etc.).

The instruments disclosed herein can be designed to be disposed of after a single use, or they can be designed to be used multiple times. In either case, however, the instrument can be reconditioned for reuse after at least one use. Reconditioning can include any combination of the steps of disassembly of the instrument, followed by cleaning or replacement of particular pieces, and subsequent reassembly. In particular, the instrument can be disassembled, and any number of the particular pieces or parts of the instrument can be selectively replaced or removed in any combination. Upon cleaning and/or replacement of particular parts, the instrument can be reassembled for subsequent use either at a reconditioning facility, or by a surgical team immediately prior to a surgical procedure. Those skilled in the art will appreciate that reconditioning of an instrument can utilize a variety of techniques for disassembly, cleaning/replacement, and reassembly. Use of such techniques, and the resulting reconditioned instrument, are all within the scope of the present disclosure.

The instruments described herein can be processed before use in a surgical procedure. First, a new or used instrument can be obtained and, if necessary, cleaned. The instrument can then be sterilized. In one sterilization technique, the instrument can be placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility. Other forms of sterilization known in the art are also possible. This can include beta or other forms of radiation, ethylene oxide, steam, or a liquid bath (e.g., cold soak). Certain forms of sterilization may be better suited to use with different portions of the instrument due to the materials utilized, the presence of electrical components, etc.

One skilled in the art will appreciate further features and advantages of the disclosure based on the above-described embodiments. Accordingly, the disclosure is not to be limited by what has been particularly shown and described, except as indicated by the appended claims. All publications and references cited herein are expressly incorporated herein by reference in their entirety.

What is claimed is:

1. A surgical instrument, comprising:
a distal end effector that includes a first jaw and a second jaw at least one of which is movable relative to the other between an open position and a closed position to clamp tissue therebetween;
a proximal housing;
an energy delivery surface operatively coupled to the distal end effector such that the energy delivery surface contacts tissue clamped between the first jaw and the second jaw when in the closed position;
a passive articulating portion disposed between the distal end effector and the proximal housing, the passive articulating portion being configured to selectively permit movement of the distal end effector relative to the proximal housing in response to an external force acting on the distal end effector;
a first locking element disposed within the proximal housing;
a second locking element disposed within the proximal housing; and
an articulation locking actuator disposed within the proximal housing, the articulation locking actuator being configured to be actuated and thereby cause the first and second locking elements and the articulation locking actuator to be pressed together such that the distal end effector is prevented from articulating relative to the proximal housing;
wherein the first locking element includes a first ring, and the second locking element includes a second ring;
wherein at least one mating feature is formed on an outer surface of the first ring;
at least one mating feature is formed on an outer surface of the second ring;
the articulation locking actuator is configured to interface with the at least one mating feature of the first ring and with the at least one mating feature of the second ring; and
with the articulation locking actuator interfaced with the at least one mating feature of the first ring and with the at least one mating feature of the second ring, the distal end effector is prevented from articulating relative to the proximal housing;
wherein an outward-facing surface of at least one of the first jaw and the second jaw has thermally insulating material formed thereon.

2. The instrument of claim 1, wherein the thermally insulating material is at least one of high-temperature polyamide, glass-filled nylon, alumina compounds, yttria-stabilized zirconia (YSZ), and poly-para-xylylene polymers.

3. The instrument of claim 1, wherein the thermally insulating material has a thickness between about 0.15 mm and about 1 mm.

4. The instrument of claim 1, wherein the thermally insulating material is sprayed onto the outward-facing surface of at least one of the first jaw and the second jaw.

5. The instrument of claim 1, wherein the thermally insulating material is overmolded onto at least one of the first jaw and the second jaw.

6. The instrument of claim 1, further comprising a cutting element operatively coupled to the distal end effector and configured to transect tissue clamped between the first jaw and the second jaw when in the closed position.

7. The instrument of claim 1, further comprising an articulation control band coupled to the distal end effector that extends proximally through the passive articulating portion and into the proximal housing.

8. The instrument of claim 7, wherein the articulation locking actuator is configured to selectively restrain the articulation control band to selectively permit movement of the distal end effector relative to the proximal housing in response to external forces acting on the distal end effector.

9. The instrument of claim 8, further comprising a second articulation control band and wherein the articulation locking actuator is configured to selectively restrain each of the articulation control band and the second articulation control band.

10. The instrument of claim 9, wherein the second articulation control band is coupled to the distal end effector and extends proximally through the passive articulating portion and into the proximal housing.

11. The instrument of claim 9, wherein the articulation locking actuator restraining each of the articulation control band and the second articulation control band prevents articulation of the distal end effector relative to the proximal housing.

12. The instrument of claim 1, further comprising a tissue clamping actuator configured to control movement of at least one of the first jaw and the second jaw of the distal end effector.

13. The instrument of claim 1, further comprising an energy delivery actuator configured to control delivery of energy to the tissue through the energy delivery surface of the distal end effector.

14. The instrument of claim 1, further comprising a first articulation band coupled to the first locking element; and
a second articulation control band coupled to the second locking element;
wherein the pressing together of the first locking element, the second locking element, and the articulation locking actuator restrains the articulation control band and the second articulation control band to prevent the distal end effector from articulating relative to the proximal housing.

15. The instrument of claim 14, wherein the articulation locking actuator being out of contact with the first locking element and the second locking element does not restrain the first articulation control band, so as to permit longitudinal translation of the first articulation control band, and does not restrain the second articulation control band, so as to permit longitudinal translation of the second articulation control band.

16. The instrument of claim 1, wherein the articulation locking actuator being out of contact with the first locking element and the second locking element permits movement of the distal end effector relative to the proximal housing in response to the external force acting on the distal end effector.

17. The instrument of claim 1, wherein the articulation locking actuator being out of contact with the at least one mating feature of the first ring and the at least one mating feature of the second ring permits movement of the distal end effector relative to the proximal housing in response to the external force acting on the distal end effector.

18. The instrument of claim 1, wherein the articulation locking actuator includes a threaded inner surface configured to interface with the at least one mating feature of the first ring and with the at least one mating feature of the second ring.

19. A surgical instrument, comprising:
- a distal end effector that includes a first jaw and a second jaw at least one of which is movable relative to the other between an open position and a closed position to clamp tissue therebetween;
- a proximal housing;
- an energy delivery surface operatively coupled to the distal end effector such that the energy delivery surface contacts tissue clamped between the first jaw and the second jaw when in the closed position;
- a passive articulating portion disposed between the distal end effector and the proximal housing, the passive articulating portion being configured to selectively permit movement of the distal end effector relative to the proximal housing in response to an external force acting on the distal end effector;
- a first articulation band that extends proximally through the passive articulating portion and into the proximal housing;
- a second articulation band that extends proximally through the passive articulating portion and into the proximal housing;
- an articulation locking actuator disposed within the proximal housing;
- wherein the articulation locking actuator is configured to move from a first position, in which the first articulation band, the second articulation band, and the articulation locking actuator are permitted to move proximally and distally relative to the proximal housing so as to permit movement of the distal end effector relative to the proximal housing in response to the external force acting on the distal end effector, to a second position, in which the first articulation band, the second articulation band, and the articulation locking actuator are prevented from moving proximally or distally relative to the proximal housing so as to prevent movement of the distal end effector relative to the proximal actuating portion in response to the external force acting on the distal end effector;
- wherein an outward-facing surface of at least one of the first jaw and the second jaw has thermally insulating material formed thereon.

20. The instrument of claim 19, wherein the articulation control band is coupled to a first locking element;
- the second articulation control band is coupled to a second locking element;
- the articulation locking actuator in the first position is out of contact with the first locking element and the second locking element to prevent movement of the distal end effector relative to the proximal housing in response to the external force acting on the distal end effector; and
- the articulation locking actuator in the second position is configured to press the first locking element and the second locking element together to permit movement of the distal end effector relative to the proximal housing in response to the external force acting on the distal end effector.

21. The instrument of claim 20, wherein the first locking element includes a ring;
- the second locking element includes a ring; and
- an inner surface of the articulation locking actuator in the second position is configured to press against an outer surface of the first ring and against an outer surface of the second ring.

* * * * *